United States Patent [19]

Ikuno et al.

[11] Patent Number: 4,901,142
[45] Date of Patent: Feb. 13, 1990

[54] VIDEO SCOPE SYSTEM

[75] Inventors: Yuji Ikuno, Ohme; Takeaki Nakamura, Hino; Yoshikazu Tojo, Hachioji; Shinichi Nishigaki, Setagaya; Hiromasa Suzuki, Akishima; Hisao Yabe, Hachioji; Jun Yoshinaga, Hino; Takeshi Yokoi, Hachioji; Kazuhiko Ohzeki, Hachioji; Masahide Kanno, Hachioji, all of Japan

[73] Assignee: Olympus Optical Co., Ltd., Tokyo, Japan

[21] Appl. No.: 169,959

[22] Filed: Mar. 18, 1988

[30] Foreign Application Priority Data

Mar. 23, 1987 [JP] Japan .................................. 62-68575
Apr. 22, 1987 [JP] Japan .................................. 62-97599
Jan. 22, 1988 [JP] Japan .................................. 62-10940

[51] Int. Cl.$^4$ .............................................. H04N 7/18
[52] U.S. Cl. ......................................... 358/98; 128/4; 128/6
[58] Field of Search ....................... 358/98; 128/4, 6

[56] References Cited

U.S. PATENT DOCUMENTS 4,349,014  9/1982  Takamatsu ............................. 128/6
4,423,436 12/1983  Kimura ................................. 358/98
4,487,489 12/1984  Takamatsu .............................. 128/6
4,601,284  7/1986  Arakawa et al. ...................... 358/98
4,638,353  1/1987  Nagasaki et al. ...................... 358/98
4,646,724  3/1987  Sato et al. ............................ 358/98
4,708,126 11/1987  Toda et al. ............................. 128/6
4,713,683 12/1987  Fujimori et al. ....................... 358/98
4,740,837  4/1988  Yanagisawa et al. .................. 358/98

Primary Examiner—John K. Peng
Attorney, Agent, or Firm—Stevens, Davis, Miller & Mosher

[57] ABSTRACT

A video scope system including a video scope in which a solid state image sensor is disposed in a distal end of an insertion to be inserted into an object under inspection and picks up an image of the inside of the object under inspection illuminated by a light fed by a light guide extending in the insertion section, a light source unit having a light source feeding a light into the light guide, and a video processor unit processing a signal supplied from the solid state image sensor to output a picture signal to be displayed on a monitor. The light source unit and the video processor unit are disposed in separate housings, respectively, and these units are connected to each other by a cable to transmit a signal therebetween.

23 Claims, 26 Drawing Sheets

FIG_1 PRIOR ART

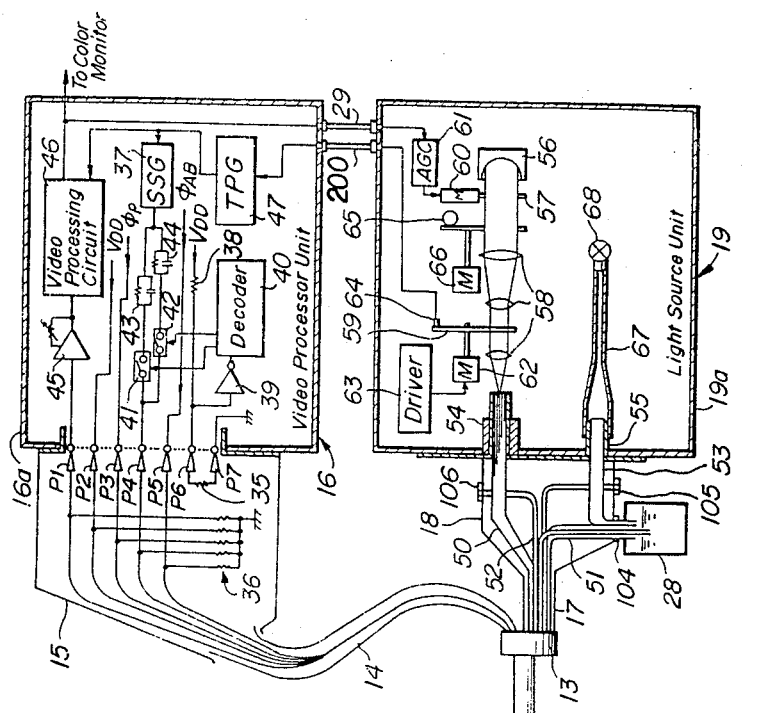
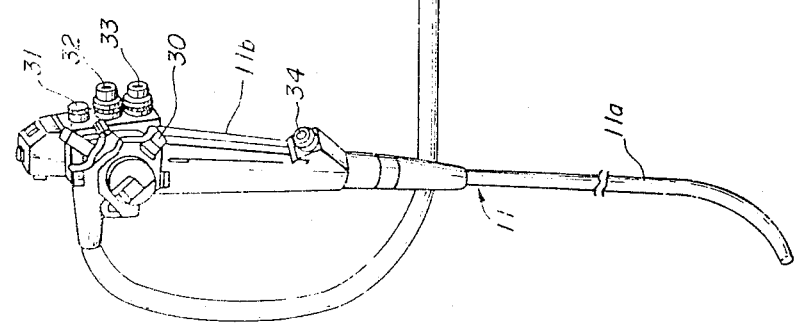
FIG. 3

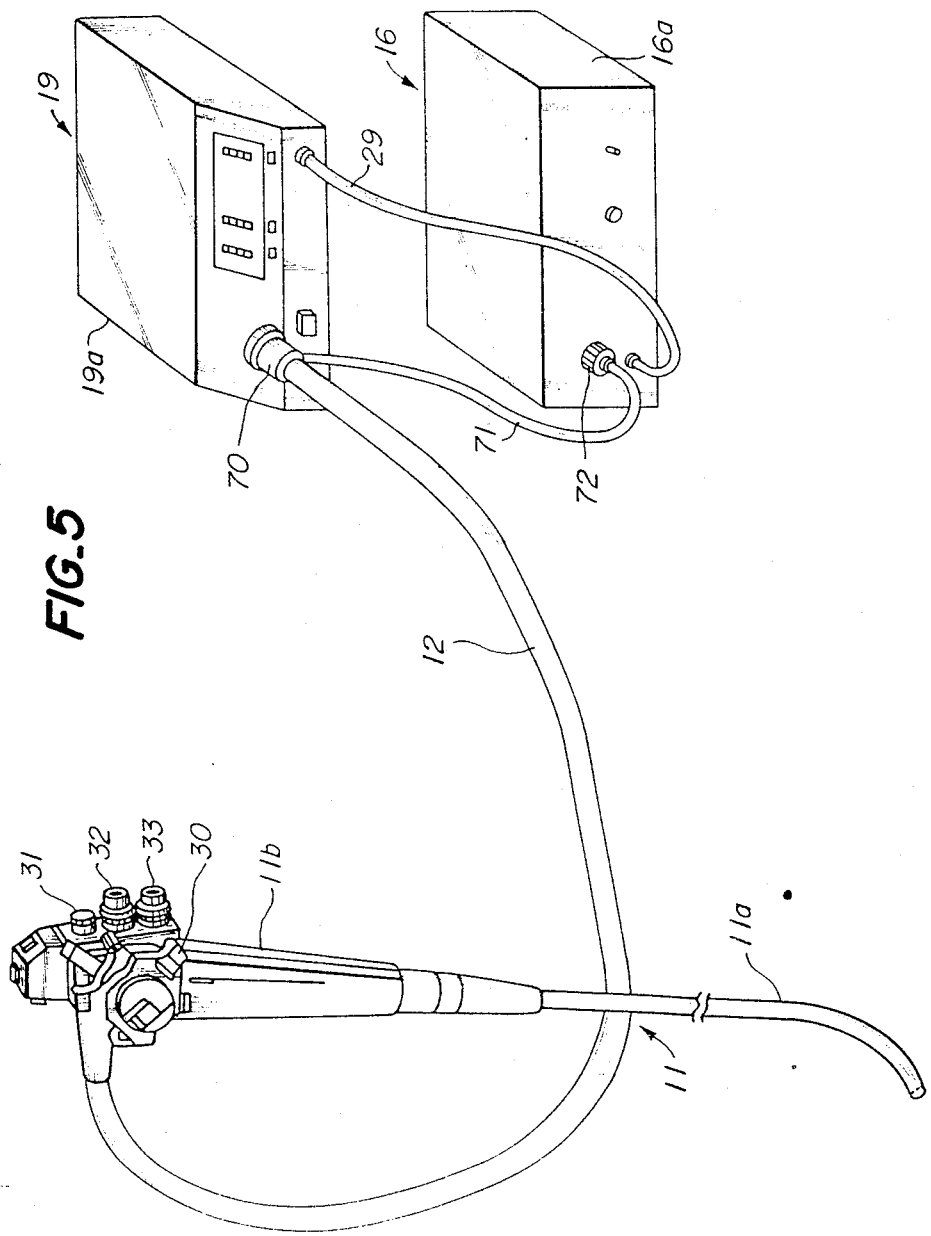

VIDEO SCOPE SYSTEM

BACKGROUND OF THE INVENTION

1. Field of the Invention

The present invention relates to a video scope system comprising an optical system disposed in a distal end of an insertion section to be inserted in an object under inspection for forming an image of the object, a solid state image sensor such as CCD, BBD, SIT and the like for picking up the image of the object, a video processor unit for processing an image signal supplied from the solid state image sensor, and a monitor for receiving the image signal to display the image of an inner portion of the object under inspection.

2. Description of the Related Art

Various types of video scope systems are already known: U.S. Patent specification No. 4,539,586, for example, discloses a video scope system as shown in FIG. 1. A video scope 1 of this video scope system has an insertion section 1a which is inserted in the object under inspection, and a handle section 1b connected to a proximal end of the insertion section 1a. An image sensor (not shown) is disposed in a distal end of the insertion section 1a, in which there are provided a light guide feeding a light for illuminating a subject under inspection, i.e., an inner wall of a cavity of a human body, an air supply tube for supplying air into the object under inspection, a water supply tube for supplying water for removing foreign matters applied on an objective lens, an inert gas tube for feeding an inert gas into the object under inspection, and a conductor bundle for supplying a driving signal to the image sensor and feeding an image signal supplied from the image sensor to a point outside the video scope 1. These light guide, air supply tube, water supply tube, gas tube, and conductor bundle are arranged in a universal cable 2 connected to the handle section 1b, and are connected to an external apparatus 4 through a connector 3. A light source unit feeding an illuminating light into the light guide, an air supply pump, and a video processor unit are arranged and housed in the external apparatus 4. The image signal supplied from the image sensor is supplied to the video processor unit of the external apparatus 4 through a lead extending through the insertion section 1a and the universal cable 2, is processed by the video processor unit in a usual manner, and then is supplied to a monitor 5 so that an image of an inner portion of the object under inspection can be displayed.

U.S. Patent specification No. 4,601,284 discloses a video scope system constructed in such a manner that an attachment including a solid stage image sensor is detachably attached to an eyepiece section provided at a handle section of a usual optical fiber scope having a light guide and an image guide, so that an endoscope image is displayed on a monitor. In this conventional system, a connector connected to a universal cord cable which is connected to the handle section, and a connector connected to a conductor bundle which is connected to an adapter, are respectively connected to sockets provided on an external apparatus housing a light source unit and a video processor unit.

In the conventional video scope system described above, since the video processor unit, the light source unit, the air supply pump and the like are all disposed in the external apparatus, heat generated by a light source lamp provided in the light source unit interferes with the proper functioning of electronic circuits provided in the video processor unit.

If a motor driving a stop for carrying out an automatic gain control for the light source unit, a motor for inserting an emergency lamp into an optical path, or a motor for rotating a color filter in the optical path in a field or frame sequential television system are provided in a housing together with the electronic circuits, the heat generated by these motors is likely to have an adverse influence on the electronic circuits, and noise generated by these motors also may affect the operation of the electronic circuits.

Further, if a part of the external apparatus malfunctions or is damaged, the external apparatus must be replaced, as a complete unit, for a new unit. Therefore, the conventional system has a drawback in that the running costs are increased, and since the operation for replacing the video processor unit is complicated and time-consuming, if the change-over of the unit must be made during the inspection of the inside portion of a patient body, the patient is subjected to unnecessary pain and anxiety, because the change-over operation cannot be made promptly.

In U.S. Patent Specification No. 4,539,586, the electrical connection, optical connection, and mechanical connection are all made through one connector 3, and thus the connector has a complicated construction and is very costly. Also, the connector must be carefully connected to and disconnected from a socket to ensure a good connection between the connector and the socket and to prevent damage thereto, and accordingly, the operation becomes complicated.

The above described problems occur not only in the video scope in which the image sensor is disposed in the distal end of the insertion section thereof, but also in a video scope system in which an image transmitted by the image guide is picked up by an image sensor disposed in a proximal end of the insertion section.

SUMMARY OF THE INVENTION

An object of the present invention is to provide a video scope system in which the electronic circuits provided in the video processor unit are effectively protected from the adverse influence of heat generated by the light source lamp disposed in the light source unit, to eliminate the above drawback of the prior art system.

The video scope system according to the present invention picks up an image of an object under inspection, the image being formed by an optical system disposed in a distal end of an insertion section inserted in the object under inspection. The video scope system comprises a video scope, a light source unit, a video processor unit, a shielding means, and an electrical connecting means.

The video scope comprises the insertion section including an image sensor for picking up the image of the object under inspection, a conductor connected to the image sensor, a first connector connected to the conductor, a light guide extending into the insertion section and having a light incident end, and a second connector holding the light incident end. The light source unit has a first socket detachably connected to the second connector, and feeds an illumination light into the light guide, and the video processor unit has a second socket detachably connected to the first connector. The video processor unit outputs a driving signal for the image sensor, and processes an image signal received from the image sensor. The shielding means thermally separates the light source unit and the video processor unit from each other, and the electrical connecting means transmits signals between the light source unit and the video processor unit.

According to the video scope system of the present invention, since the light source unit and the video processor unit are separated from each other by the shielding means, heat generated by the light source unit can not have an adverse influence on the video processor unit.

In a preferred embodiment of the present invention, the light source unit and the video processor unit are housed in different casings, respectively, and these casings are housed in a common housing so that the light source unit and the video processor unit can be replaced independently, whereby the change-over is carried out promptly and easily and thus the running costs are reduced.

In another preferred embodiment of the present invention, since the video processor unit for processing an image signal and the light source unit for emitting the illumination light have entirely separate constructions, these units can be separately replaced by new units, and thus the cost is reduced because the change-over is easy and can be carried out in a very sort time. Further, noise or heat generated by the motor disposed in the light source unit have little or no affect on the electronic circuits in the video processor unit. Also, as the separate connectors are provided for the video processor unit and the light source unit, the constructions of these connectors are simple and the connecting and disconnecting thereof made easy.

BRIEF DESCRIPTION OF THE DRAWINGS

The present invention will be more fully understood from the description of the preferred embodiments of the invention set forth below, together with the accompanying drawings, in which:

FIG. 3 is a view showing details of the construction of the video processor unit and the light source unit of the first embodiment;

FIG. 5 is a perspective view of a general construction of a second embodiment of the video scope system according to the present invention;

DESCRIPTION OF THE PREFERRED EMBODIMENTS

Figure 1:
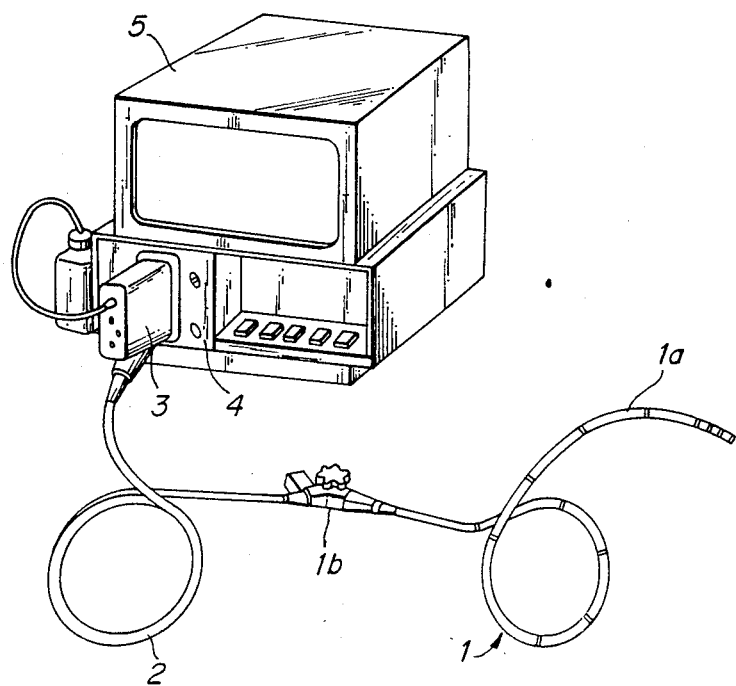
FIG. 1 is a perspective view showing the general construction of a prior art video scope system.
Figure 2:
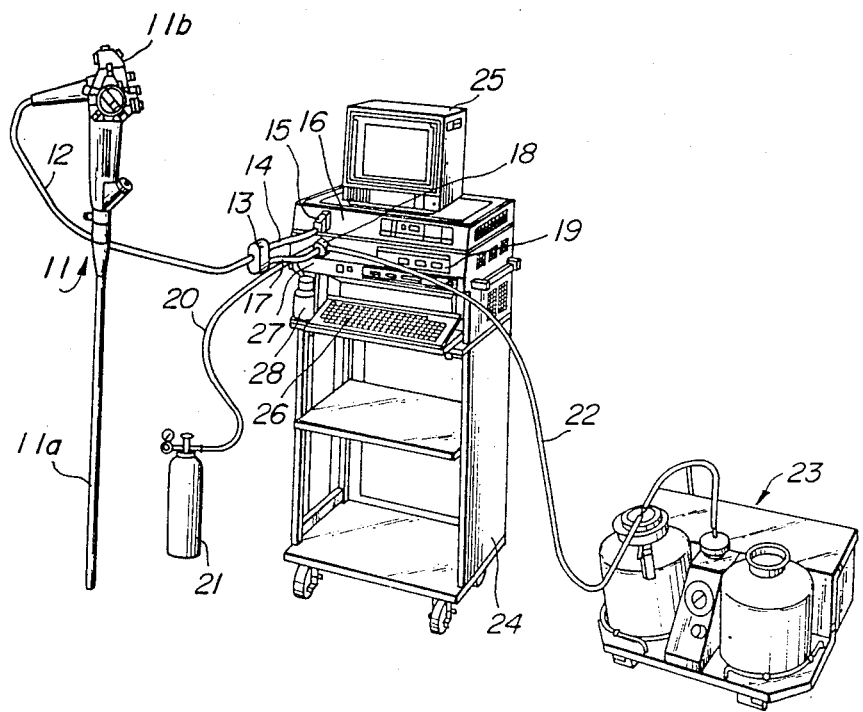
FIG. 2 is a perspective view of a general construction of a first embodiment of the video scope system according to the present invention.

FIG. 2 shows a general construction of a first embodiment of the video scope system according to the present invention. A video scope 11 has an insertion section 11a to be inserted into an object under inspection, and a handle section 11b provided with various devices. An image sensor such as a CCD and the like is provided in the distal end of the insertion section 11a. The insertion section 11a also contains a conductor bundle connected to the image sensor, a light guide for guiding illumination light, a water supply tube, an air supply tube, and a forceps channel for inserting and removing a forceps. The handle section 11b is connected to a universal cable 12 in which the conductor bundle, the light guide, the air supply tube, the water supply tube, an inert gas supply tube, and a suction tube are housed, and which extends to a branch section 13. At the branch section 13, the conductor bundle, the light guide, the air supply tube, the water supply tube are branched from the cable 12. Namely, the conductor bundle is connected to a video processor unit 16 through an electric cable 14 and a connector 15, and the light guide, the air supply tube, and the water supply tube are connected to a light source unit 19 through a universal cable 17 and a connector 18, which is connected through a tube 20 to a gas cylinder 21 filled with an inert gas and to a suction apparatus 23 through a tube 22. The video processor unit 16 and the light source unit 19 are housed in separate housings mounted on a rack 24, on which a color monitor 25, an input device 26 including a keyboard, a video recorder 27, and a tank 28 for supplying water are also mounted. The video processor unit 16 and the light source unit 19 are connected to each other by an electric cable.

FIG. 3 shows the details of the construction of the handle section 11b of the video scope, the video processor unit 16, and the light source unit 19. The handle section 11b is provided with a handle 30 for moving the distal end of the insertion section 11a up and down or right and left, and on an upper portion of the handle section 11b are provided an inert gas supply piston 31, a suction piston 32, and a water supply piston 33. An opening 34 for inserting and removing a forceps is formed in a lower portion of the handle section 11b.

When the inert gas supply piston 31 is operated, an inert gas is supplied into the object under inspection through the air supply tube in the insertion section 11a, and when the suction piston 32 is operated, the forceps channel and the suction tube are communicated with each other so that a suction operation is carried out. The air and water supply piston 33 is provided with an open hole, and an air supply is carried out by selectively closing the hole with a finger, and if the piston is pressed in, a water supply is carried out.

An inside portion of the connector 15 detachably connected to a socket 16b provided in a housing 16a of the video processor unit 16 is provided with a scope length discriminating resistor 35 having a resistance value corresponding to a scope length (a length from the connector 15 to the distal end of the insertion section 11a), electrostatic charge protection resistors 36 for preventing damage to the image sensor by an electrostatic charge from a human body on an article which may come into contact with the leads connected to the image sensor or one of contact pins P1 through P5 connected to that leads. The scope length discriminating resistor 35 is connected to the video processor unit 16 through pins P6 and P7. The video processor unit 16 is provided with a standard signal generating circuit (SSG) 37 for driving the CCD image sensor. A voltage determined by a ratio of the scope length discriminating resistor 35 and a reference resistor 38 is sensed by a comparator 39, and the output thereof is supplied to a decoder 40. One of switches 41 and 42 is closed by an output signal of the decoder 40, and therefore, a signal output from the standard signal generating circuit 37 for driving the CCD image sensor is supplied to the image sensor through a matching circuit 43 or 44 corresponding to the scope length. VDD, $\Phi_P$, and $\Phi_{AB}$ are applied to image sensor through contacts P2, P3, and P5, respectively.

An image signal output from the image sensor and supplied through the pin P1 is amplified by a preamplifier and then is supplied to a video processing circuit 46 in which a predetermined process is carried out to produce a color television signal which is supplied to the color monitor 25 (refer to FIG. 2), so that a color image is displayed on the monitor. As will be described later, in this embodiment, since a field or frame sequential system of R, G, and B is applied, the video processing circuit 46 carries out a signal process appropriate to the system. Note, as such a video process circuit per se is well known, a detailed explanation of the circuit is omitted herein.

The connector 18 detachably connected to a socket disposed in the housing 19a of the light source unit 19 is provided with a light guide 50, an air supply tube 51, a water supply tube 52, and a pipe 53 communicated with a water tank 28, and further provided with an inert gas supply tube and a suction tube. The light source unit 19 is equipped with a socket 54 for receiving an end of the light guide 50 and a socket 55 for receiving the pipe 53 communicating with the water tank 28. Namely, the light source unit 19 is equipped with two sockets. The light source unit 19 is further provided with a high intensity lamp 56, a stop 57 for controlling a quantity of light fed into the light guide 50, a condenser lens system 58, and a rotary filter 59 having red, green, and blue filter regions. The light source unit 19 is also provided with a motor 60 for controlling an aperture of the stop 57, and an automatic gain control circuit (AGC) 61 for sensing an output image signal level of the video processing circuit 46 and supplying a driving signal to the motor 60 so that a gain of the image signal has a predetermined constant value. Namely, the gain of the image signal is automatically controlled. The rotary filter 50 is connected to a motor 62, and motor drive circuit (driver) 63 for driving the motor 62 is provided in the light source unit 19. A sensor 64 is disposed in the light source unit 19 for sensing a mark formed on a frame of the rotary filter 59, to detect a filter region of the filter 59 located in an optical path of the illuminating light so that a signal process synchronized with a color of the filter region located in the optical path is carried out in the video processing circuit 46. Further, the light source unit 19 is provided with an emergency lamp 65 which is automatically turned ON when a defect in the lighting is sensed, to prevent a sudden loss of light at the surface of monitor when a malfunction of the light source lamp 56 occurs. A motor 66 is provided for inserting the emergency lamp 65 into the optical path. The socket 55 receiving the pipe 53 is connected to an air supply pump 68 through a pipe 67.

As described above, in the present invention, in order to carry out an automatic gain control of an image signal and a signal processing in synchronized with the rotary filter 59, a signal must be transmitted between the video processor unit 16 and the light source unit 19, and therefore, signal cables 29 and 200 are connected between the video processor unit 16 and the light source unit 19. Therefore, if either the video processor unit 16 or the light source unit 19 malfunctions, the cables 29 and 200 must be disconnected before the malfunctioning unit is replaced by a new unit. This operation is very easy, and enables a quick change-over of either unit.

Since the connector 15 for connecting the conductor bundle, which is connected to the image sensor, to the video processor unit 16 is separate from the connector 18 for optically connecting the light guide 50 to the light source lamp 56, the constructions of these connectors 15 and 18 are simple, and the connectors 15 and 18 are easily connected and disconnected. Since the video processor unit 16 and the light source unit 19 are housed in separate housings 16a and 19a, respectively, any influence on the electronic circuit of the video processor unit 16 by noise generated by the various motors disposed in the light source unit or heat generated by the light source lamp 56 is reduced, so that a stable color image having a high image quality can be displayed on the color monitor.

Figure 4A:
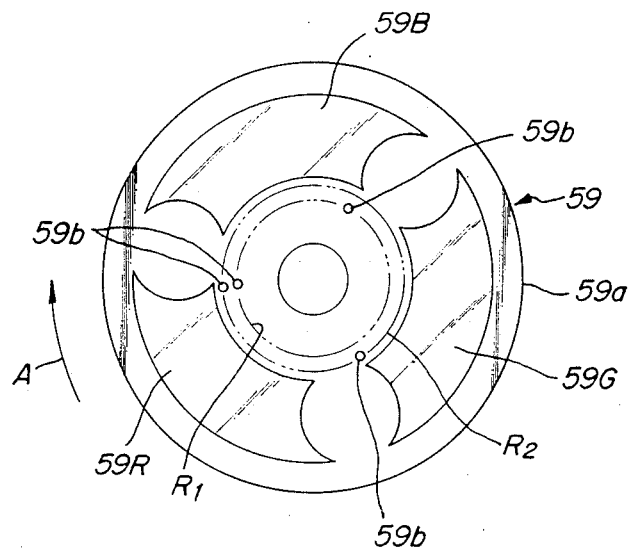
FIG. 4A is a plan view showing details of the construction of a rotary filter.
Figure 4B:
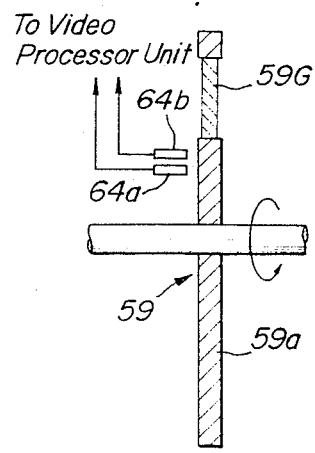
FIG. 4B is a sectional view of the rotary filter.

FIGS. 4A and 4B show a construction of the rotary filter 59 provided in the light source unit 19. In this embodiment, a red color filter 59R, a blue color filter 59B, and a green color filter 59G are provided on a disk 59a and arranged in that order in the direction of rotation of the disk 59a shown by an arrow A. Each color filter is provided with marks 59b, so that a sensor 64 comprising for example, a pair of photo reflectors 64a and 64b, optically senses the marks 59b to detect the color of the filter region located in the optical path. Namely, the photo reflectors 64a and 64b are disposed in such a manner that one photo reflector 64a scans along an inside circular locus $R_1$ and the other photo reflector 64b scans along an outside circular locus $R_2$. The mark 59b indicating the red filter 59R is provided on the outside circular locus $R_2$, and the mark 59b indicating the green filter 59G is provided on the inside circular locus $R_1$. The blue filter 59B is indicated by two marks 59b, one mark being provided on each of the outside and inside circular loci R₂ and R₁. Namely, the color of the filter is identified by signals generated from the photo reflectors 64a and 64b.

Figure 4C:
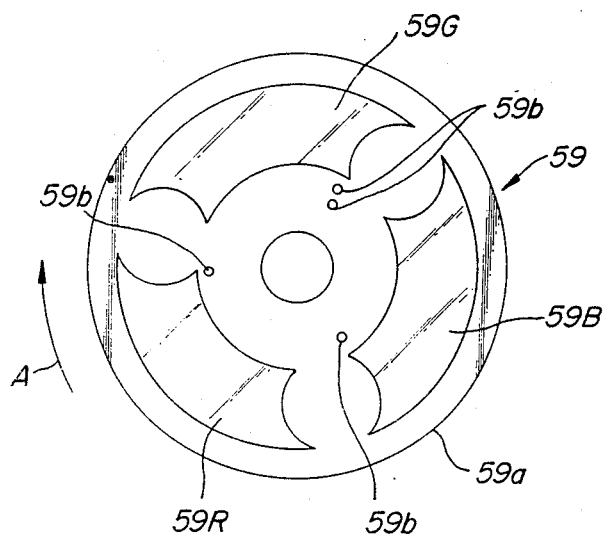
FIG. 4C is a plan view of another rotary filter.

In the embodiment described above, although the color filters provided on the rotary filter 59 are arranged so that the red, blue and green filters 59R, 59B and 59G appear in that order along the direction of rotation of the disk 59a, the order of the color filters may be alternatively arranged as shown in FIG. 4C. A filter allowing all of the visible light to pass therethrough, or one having an aperture, can be provided instead of the green filter in the red, blue and green filters, and instead of the red, blue, and green filters, complementary color filters of the three filters can be provided.

As shown in FIG. 3, the sensor 64 outputs a signal representing a rotational phase of the rotary filter 59, and this output signal is supplied through the cable 200, to a timing pulse generating circuit (TPG) 47 provided in the video processor unit 16, so that a timing pulse synchronized with the appropriate color filter is generated. The timing pulse is supplied to the standard signal generating circuit 37 for driving the CCD image sensor, and to the video processing circuit 46 so that a signal process synchronized with the rotary filter 59 is carried out.

Figure 6:
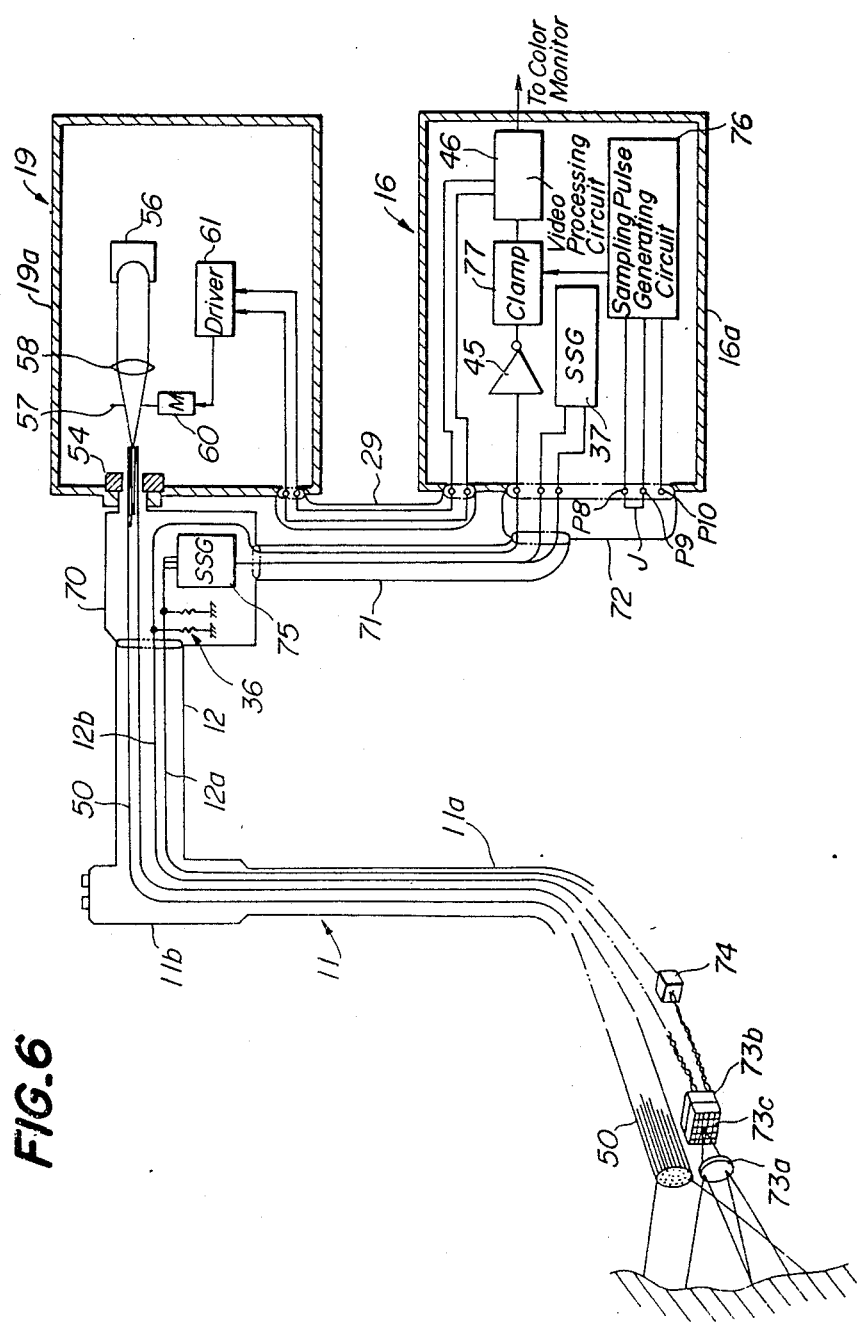
FIG. 6 is a view showing details of the construction of the second embodiment.

FIGS. 5 and 6 show a construction of a second embodiment of the video scope system according to the present invention. Parts in the second embodiment corresponding to those in the first embodiment are shown by the same reference numerals as in the first embodiment. The construction of the video scope 11 is basically the same as that of the first embodiment, except that the water supply tube and air supply tube are not provided in the second embodiment, and therefore, only the conductor bundle and the light guide are disposed in the universal cable 12 connected to the handle section 11b of the video scope 11. In this embodiment, the universal cable 12 is connected to the light source unit 19 through a connector 70, and the conductor bundle is connected to the video processor unit 16 through a separate cable 71 and a connector 72. The video processor unit 16 and the light source unit 19 are connected to each other by a cable 29 detachably connected to both units.

As shown on the left side of FIG. 6, on an enlarged scale, an object lens 73a, an image sensor 73b, and a buffer amplifier 74 for a picture signal are disposed in the distal end of the insertion section 11a of the video scope 11, and a mosaic color filter 73c is disposed on a front surface of the image sensor. A socket 54 for receiving the light guide 50, a light source lamp 56, a condenser lens 58, a variable stop 57, a motor 60 for driving the stop 57, and an automatic gain control circuit 61 for generating a motor driving signal according to a level of a picture signal, are provided in the light source unit 19. As in the first embodiment, the automatic gain control circuit 61 is connected to the video process circuit 46 through the cable 29, for carrying out an automatic gain control.

Electrostatic charge protection resistors 36, and a CCD driver 75 for generating a driving signal for the image sensor 73b are provided in the socket 70 connected to the universal cable 12. These resistors 36 and CCD driver 75 are connected to the video processor unit 16 through the cable 71. Namely, the CCD driver 75 is connected to the standard signal generating circuit 37 for driving the CCD, and the electrostatic charge protection resistors 36 are connected to the preamplifier 45. The connector 72 is provided with three pins P8 through P10, for discriminating a scope length, so that eight scope lengths can be discriminated by a selective short-circuit between the pins by a jumper J. A sampling pulse generating circuit 76 connected to the pins P8 through P10 is provided in the video processor unit 16, and a phase of the sampling pulse is adjusted according to the scope length, and accordingly, a signal generated by the circuit 76 controls a clamp circuit 77 connected to an output of the pre-amplifier 45 so that the picture signal from the clamp circuit has a predetermined level, regardless of the scope length.

Figure 7:
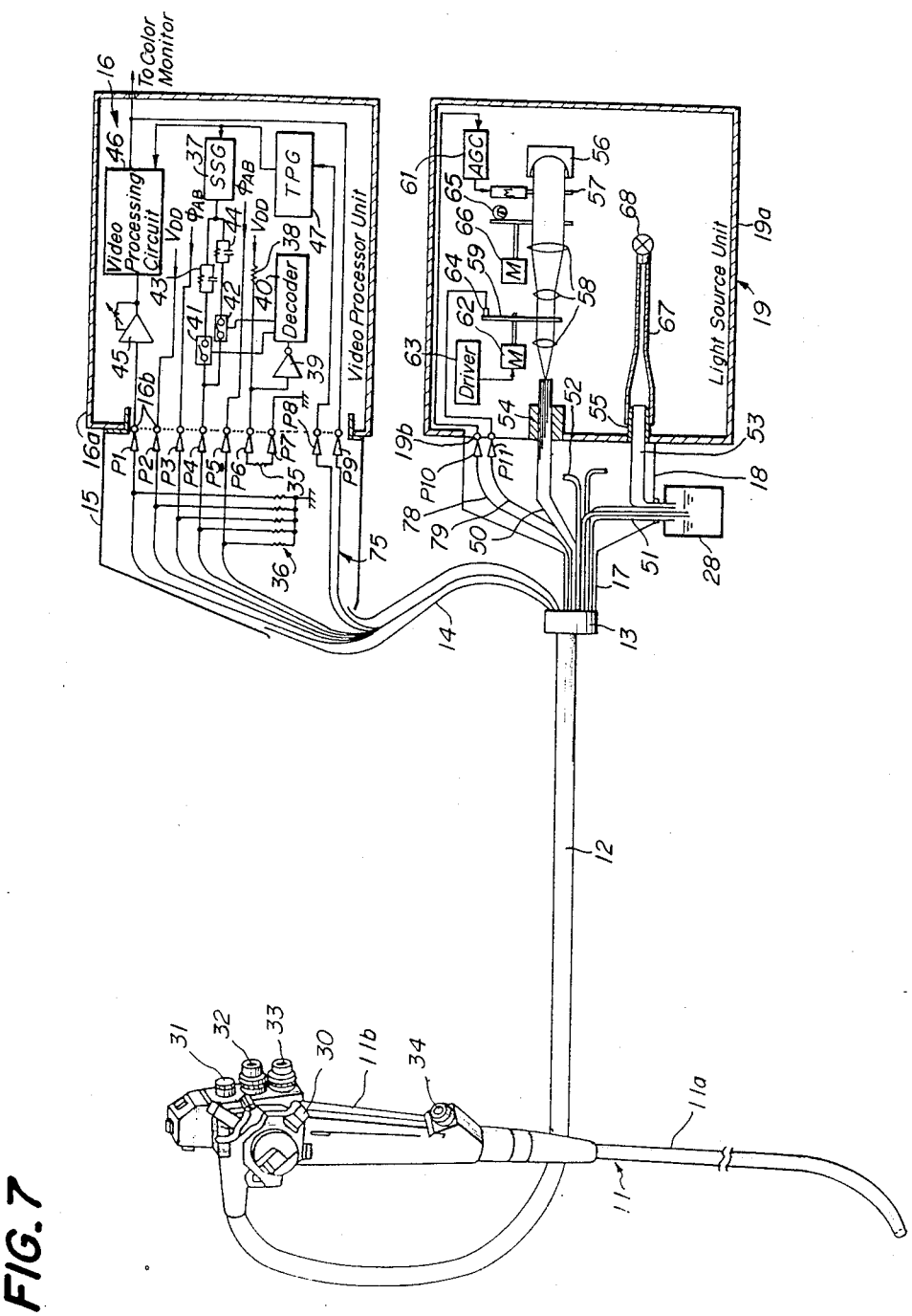
FIG. 7 is a view showing a third embodiment of the video scope system according to the present invention.

FIG. 7 shows a third embodiment of the video scope system according to the present invention. Parts in the third embodiment corresponding to those shown in the above embodiments are shown by the same reference numerals as in the above embodiments, and thus a detailed explanation of such parts is omitted. In also this third embodiment, for transmitting a signal between the video processor unit 16 and the light source unit 19, to carry out an automatic gain control for a picture signal and carry out a signal process synchronized with the rotary filter 59, a socket 16b of a video processor unit 16 and a socket 19b of a light source unit 19 are provided with socket terminals, respectively, and connectors 15 and 18 are provided with pin terminals P1 through P9, P10 and P11 corresponding to those socket terminals. The pin terminals P8 and P10 are connected to each other by a cable 78, and the pin terminals P9 and P11 are connected to each other by a cable 79. Namely, the video processor unit 16 and the light source unit 19 are electrically connected to each other by a branch cable 14, a branch section 13, and a branch cable 17. Accordingly, the connector 15 is connected to the socket 16b of the video processor unit 16 and the connector 18 is connected to the socket 19b of the light source unit 19, so that the video processor unit 16 and the light source unit 19 are electrically connected to each other to enable a signal to be transmitted therebetween.

According to this embodiment, since the video processor unit 16 and the light source unit 19 are separate units, if one unit malfunctions, only the malfunctioning unit need be replaced, and thus the change-over is quick and easy. Also, since the connector 15 for connecting the conductor bundle connected to the image sensor to the video processor unit 16 is constructed separately from the connector 18 for optically connecting the light guide 50 to the light source unit 19, the constructions of these connectors 15 and 18 are very simple, and the connecting and disconnecting thereof becomes easy. Further, since the video processor unit 16 and the light source unit 19 are electrically connected by these connectors 15 and 18, operation of the system is simplified. Furthermore, since the video processor unit 16 and the light source unit 19 are housed in separate housings 16a and 19a, respectively, the influence of heat generated by the light source lamp 56 provided in the light source unit 19 and noise generated by various motors on the electronic circuits of the video processor unit 16 is reduced, and thus an image having a high quality and a stable color reproducibility can be displayed on a color monitor 25.

Figure 8:
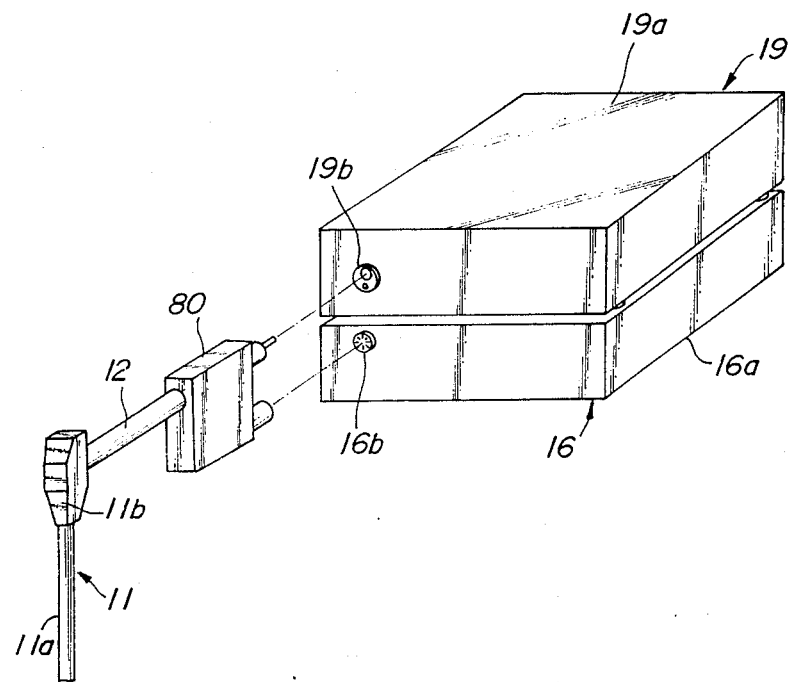
FIG. 8 is a view showing a fourth embodiment of the video scope system according to the present invention.

FIG. 8 shows a construction of a fourth embodiment of the video scope system according to the present invention. Also in this embodiment, as in the above embodiments, although a video processor unit 16 and a light source unit 19 are provided in separate housings 16a and 19a, respectively, these housings have the same dimensions on the horizontal plane, so that one housing can be stacked on top of the other housing. The sockets 16b and 19b are located on the housings 16b and 19b in such a manner that, when these housings 16a and 19a are stacked one on top of the other, the sockets 16b and 19b are aligned with each other, and thus one common connector 80 can be used for both sockets at the same time. The video processor unit 16 and the light source unit 19 are electrically connected by a cable extending in the connector 80.

Also, in this embodiment, electronic circuits provided in the video processor unit 16 are effectively protected from the influence of heat generated by the light source unit lamp 56 provided in the light source unit 19 and noise generated by motors. Further, in this embodiment, since the connector 80 is provided commonly for the video processor unit 16 and the light source unit 19, the connecting and disconnecting operations become even more easy.

Figure 9:
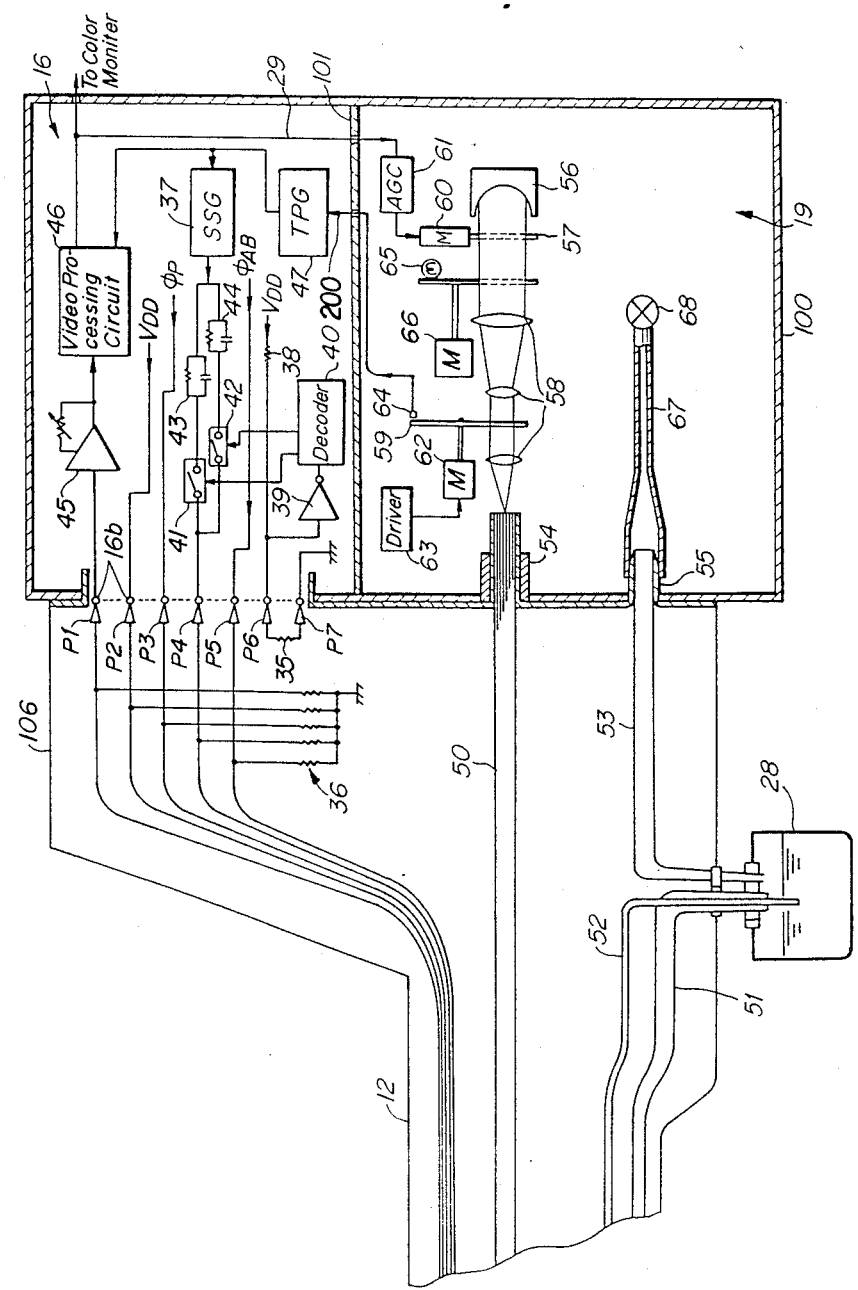
FIG. 9 is a view showing a fifth embodiment of the video scope system according to the present invention.
Figure 10:
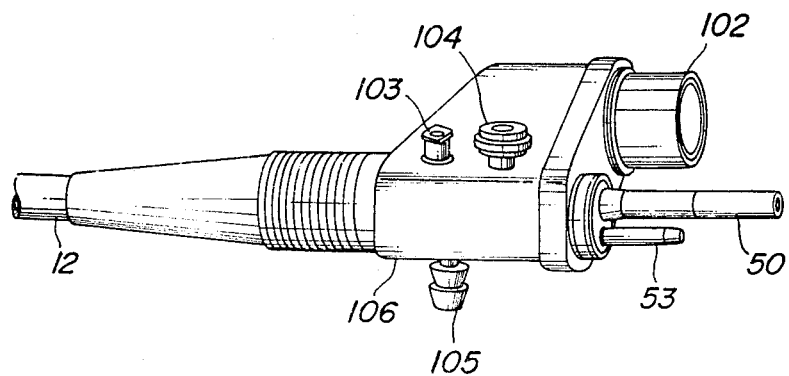
FIG. 10 is a view showing a construction of a connector of the fifth embodiment.

FIGS. 9 and 10 show a construction of a fifth embodiment of the video scope system according to the present invention. In this embodiment, a video processor unit 16 and a light source unit 19 are disposed in the same housing 100, and these two units 16 and 19 are separated by a metal shielding plate 101 having a thermal and electrical shielding effect. A connector 106 is connected to a universal cable 12 connected to a handle section of the video scope, and accordingly, an electrical connection, optical connection, and hydraulic connection are all made by this connector 106. FIG. 10 is a perspective view showing a construction of the connector 106. A jack including pins P1 through P7 connected to a conductor bundle, an end of a light guide 50, and an end of pipe 55 are provided on an end face of the connector 106 and project therefrom. The connector 106 is provided with a mouthpiece 103 connected to a water supply tank, a mouthpiece 104 connected to a gas cylinder, and a mouthpiece 105 connected to a suction device.

In this embodiment, a cable 29 for supplying a picture signal from a video processing circuit 46 of the video processor unit 16 to an automatic gain control circuit 61 of the light source unit 19, and a cable 200 for supplying a signal from the sensor 64 of the light source unit 19 to a standard signal generating circuit 47 for driving the CCD of the video processor unit 16, are extended through the shielding plate 101.

Figure 11:
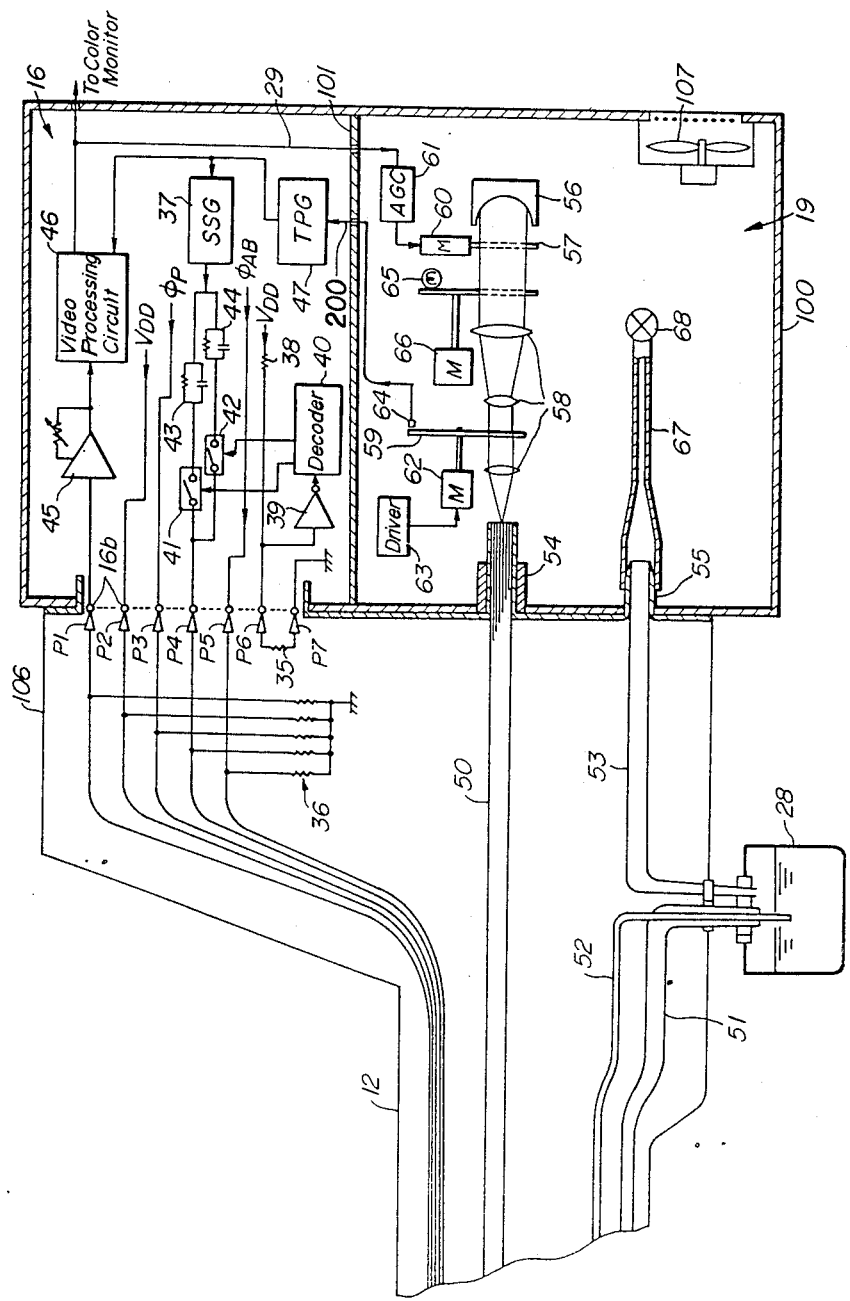
FIG. 11 is a view showing a construction of a modification of the embodiment shown in FIG. 10.

FIG. 11 shows a modification of the embodiment shown in FIG. 9. This modification is constructed in such a manner that a cooling fan 107 for cooling a lower space of the housing 100 in which the light source unit 19 is housed is provided so that air heated by the light source lamp 56 is forcibly ejected outside the housing 100. In this case, an opening for sucking air into the lower space of the housing 100 from outside may be formed in a lower portion of the housing 100 or in an upper portion housing the video processor unit 16. Especially, in the latter case, preferably an opening allowing a flow of air from the upper space to the lower space is formed in a part of the shielding plate 101.

Figure 12:
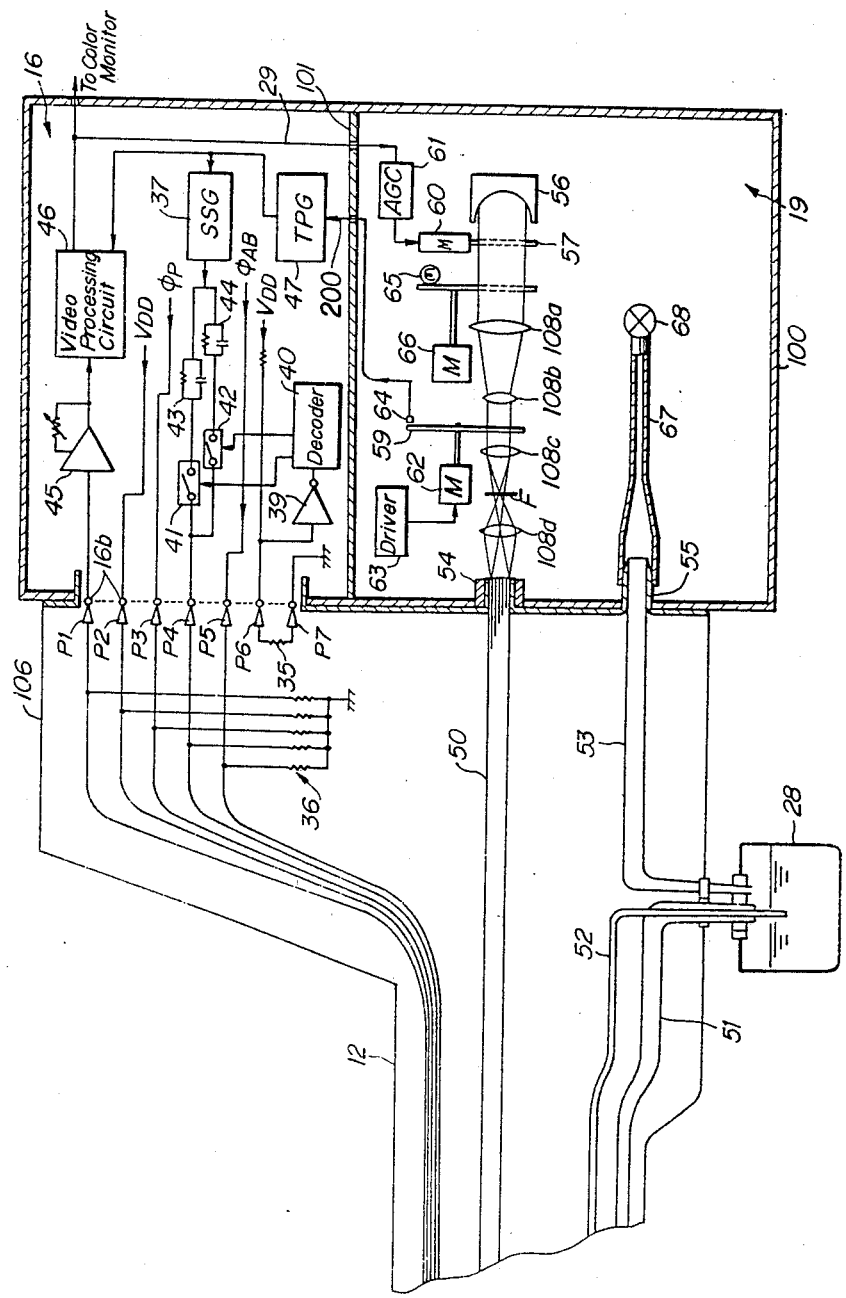
FIGS. 12, 13, and 14 are views showing constructions of other modifications of the embodiment shown in FIG. 9.

FIG. 12 shows a construction of a modification of the embodiment shown in FIG. 9. The construction is the same as that shown in FIG. 9 except for the lens system of the light source unit 19. In this modification, light emitted from the light source unit 56 and restricted to an appropriate quantity of light by the stop 57 is converged to a certain extent by a first lens 108a, and then changed to a substantially parallel ray by a second lens 108b. Then, after the light has passed through a filter 59, the light is converged by a third lens 108c to form an image of the light source lamp 56 at the focal point F. Further, a fourth lens 108d is provided in such a manner that the focal point near the object under inspection is located substantially adjacent to the focal point F, to ensure that the maximum quantity of light is fed into an incident end face of the light guide 50.

Figure 13:
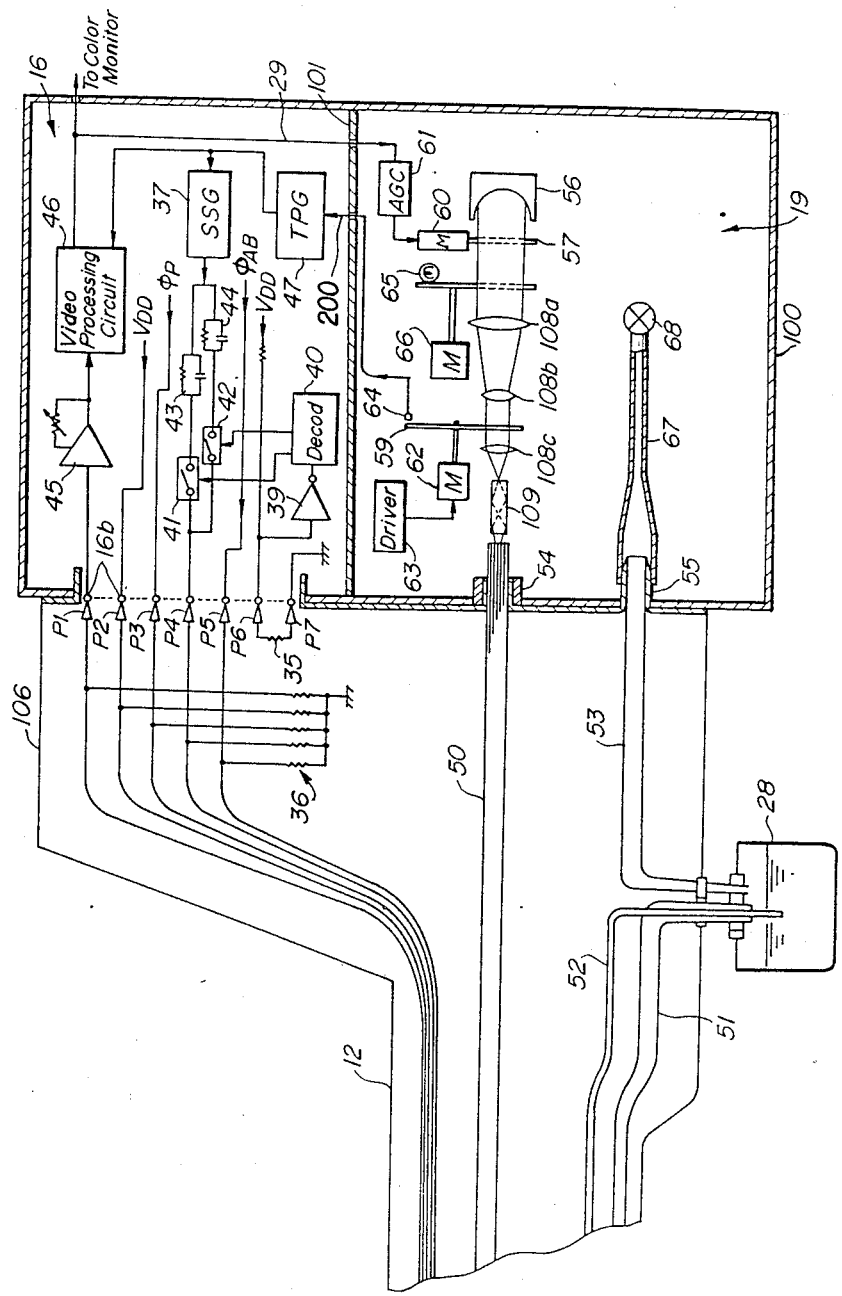

FIG. 13 shows a construction of a modification of the embodiment of FIG. 12. In this modification, only the construction of the optical system is different from that of the embodiment shown in FIG. 12. Namely, in this embodiment, light converged by the third lens 108c is fed into a rod lens 109, and the light from the rod lens 109 is fed into an incident face of the light guide 50, and thus the light is effectively fed into the light guide 50.

Figure 14:
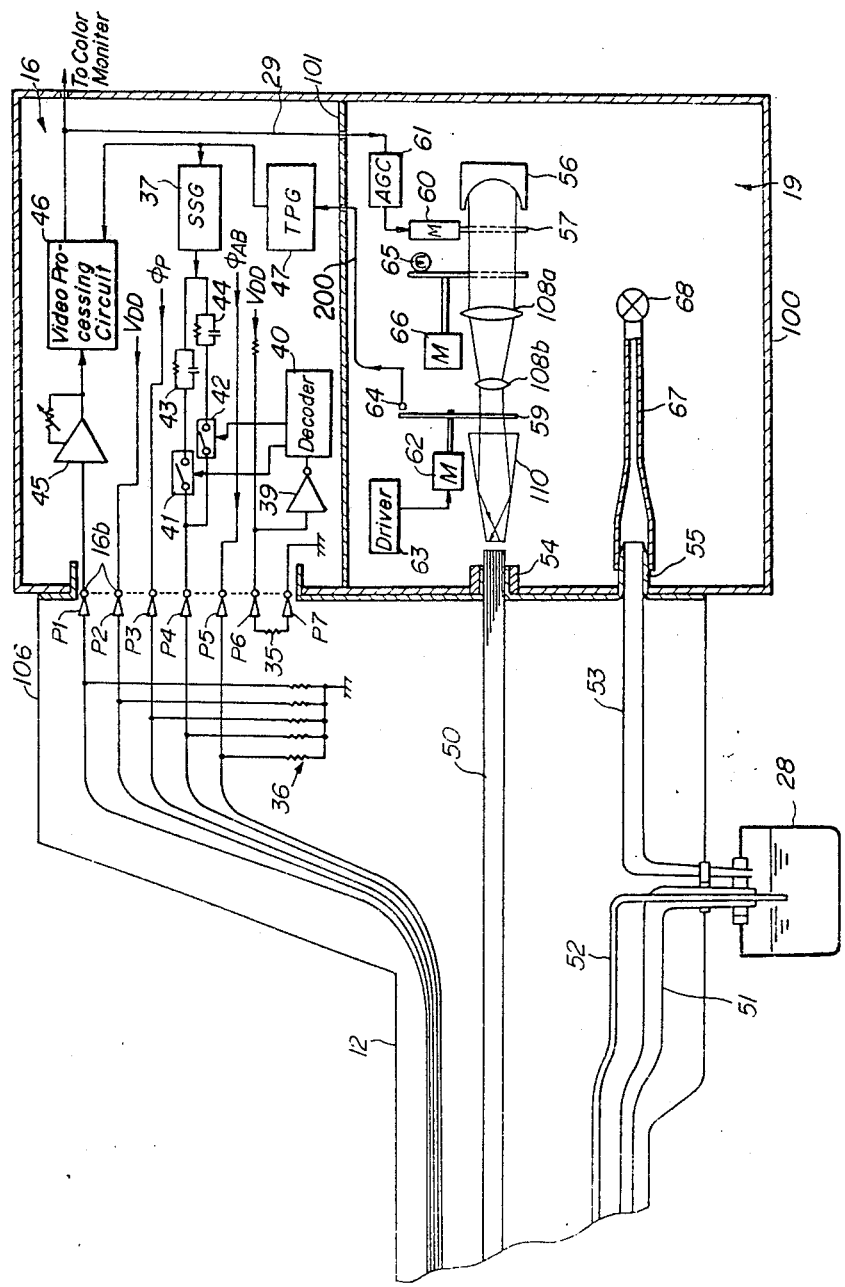

FIG. 14 shows a construction of another modification of the embodiment of FIG. 12. In this modification, only the construction of the optical system of the light source unit is different from that shown in FIG. 12. Namely, in this embodiment, parallel light emanating from the first and second lenses 108a and 108b is passed through the filter 56 and is made incident upon a rod lens 110 in the shape of a truncated cone, a diameter of the incident end of which is approximately the same as the diameter of the incident light, and a diameter of the light exit end of which is approximately the same as the diameter of the light guide 50. By using such a rod lens 110, the efficiency of the incidence of light into the light guide 50 is increased, and so-called burning caused by illumination of converged light on the incident face of the light guide 50 is effectively prevented.

Figure 15:
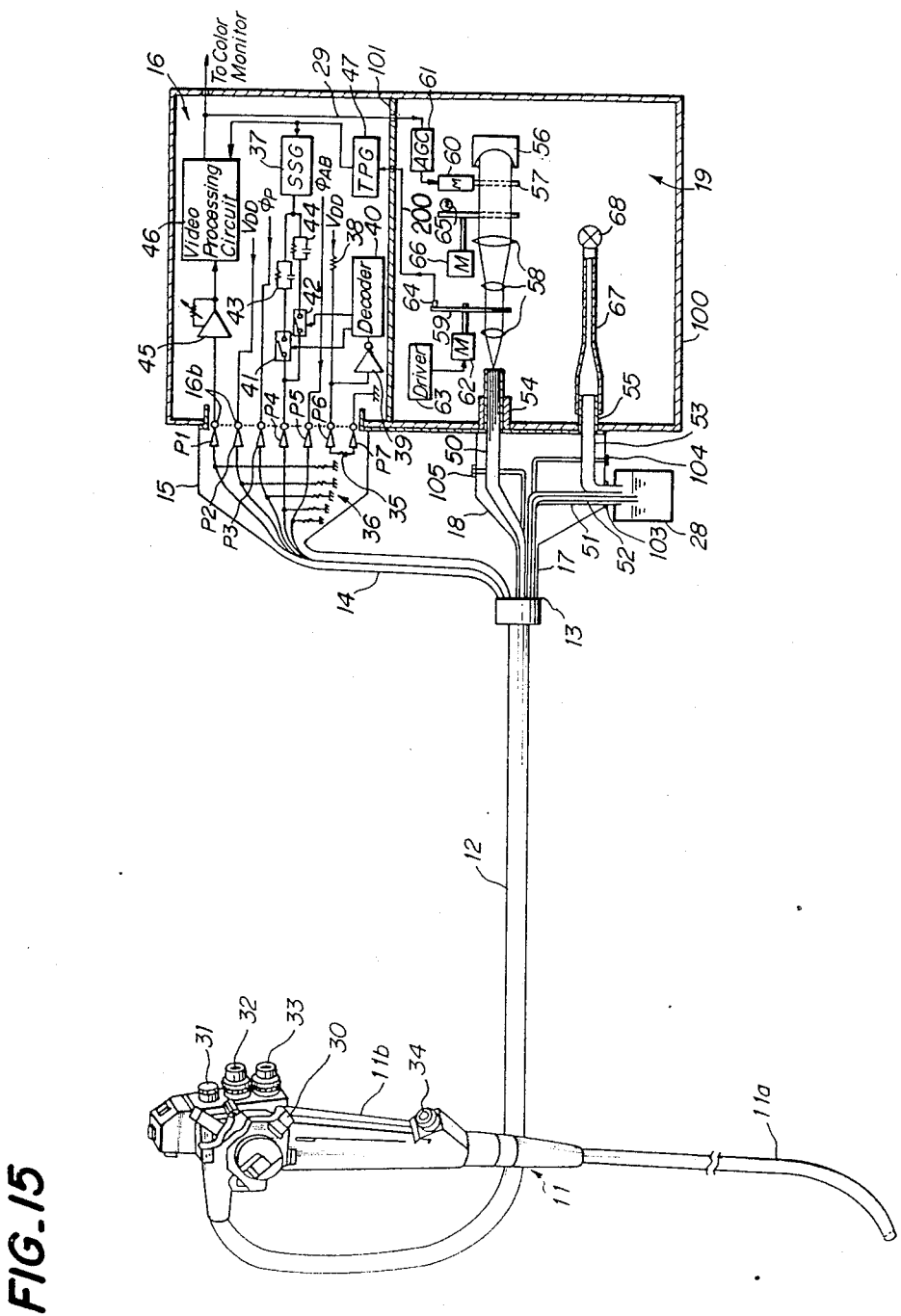
FIG. 15 is a view showing a construction of a sixth embodiment of the video scope system according to the present invention.
Figure 16:
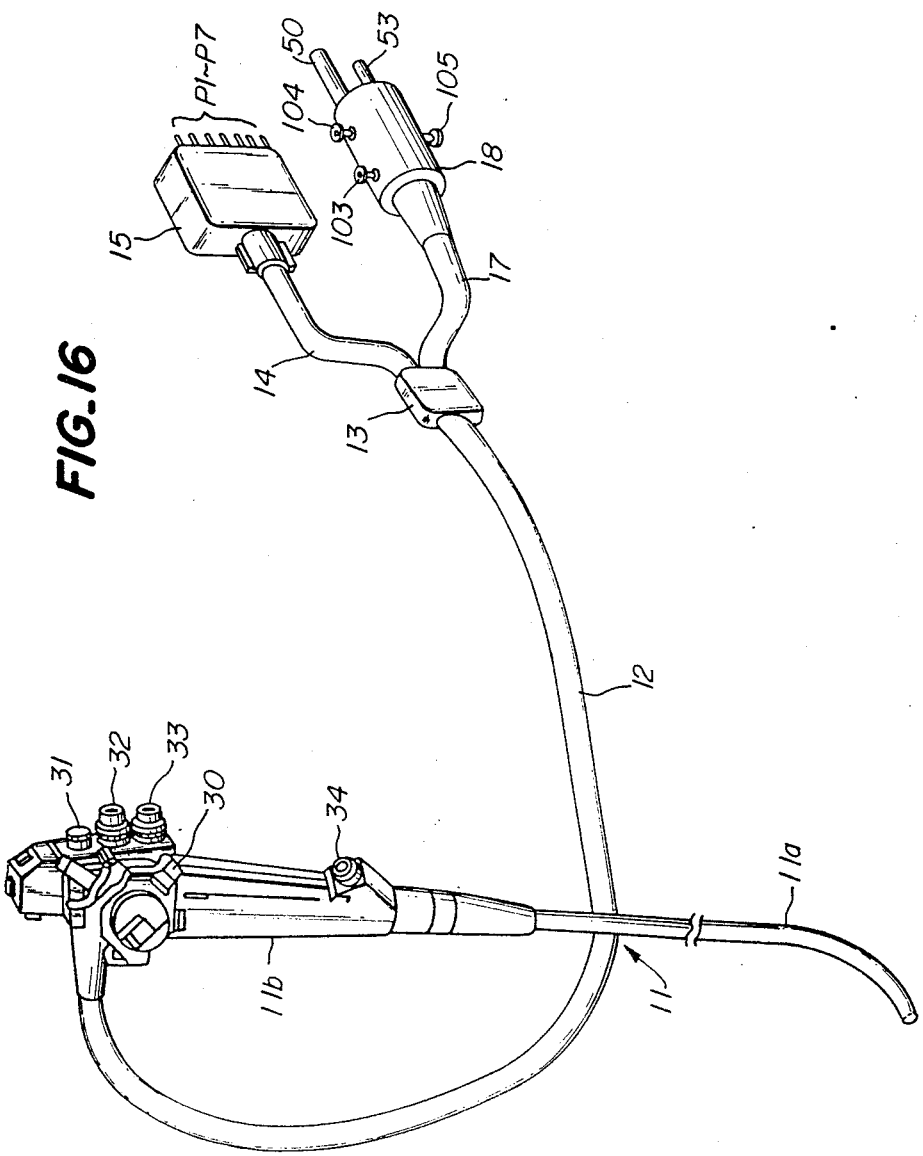
FIG. 16 is a view showing a connector of the sixth embodiment shown in FIG. 15.

FIGS. 15 and 16 show a sixth embodiment of the video scope system according to the present invention. In the embodiments of FIGS. 9 through 14, the video scope 11 and the housing 100 are connected to each other by a single connector 106, but in this embodiment, as shown in FIG. 16, the universal cable 12 is connected to the branch section 13, the conductor bundle is connected to the connector 15 through the cable 14, and the light guide 50, the air supply tube 51, and the water supply tube 52 are connected to the connector 18 through the universal cable 17.

Figure 17:
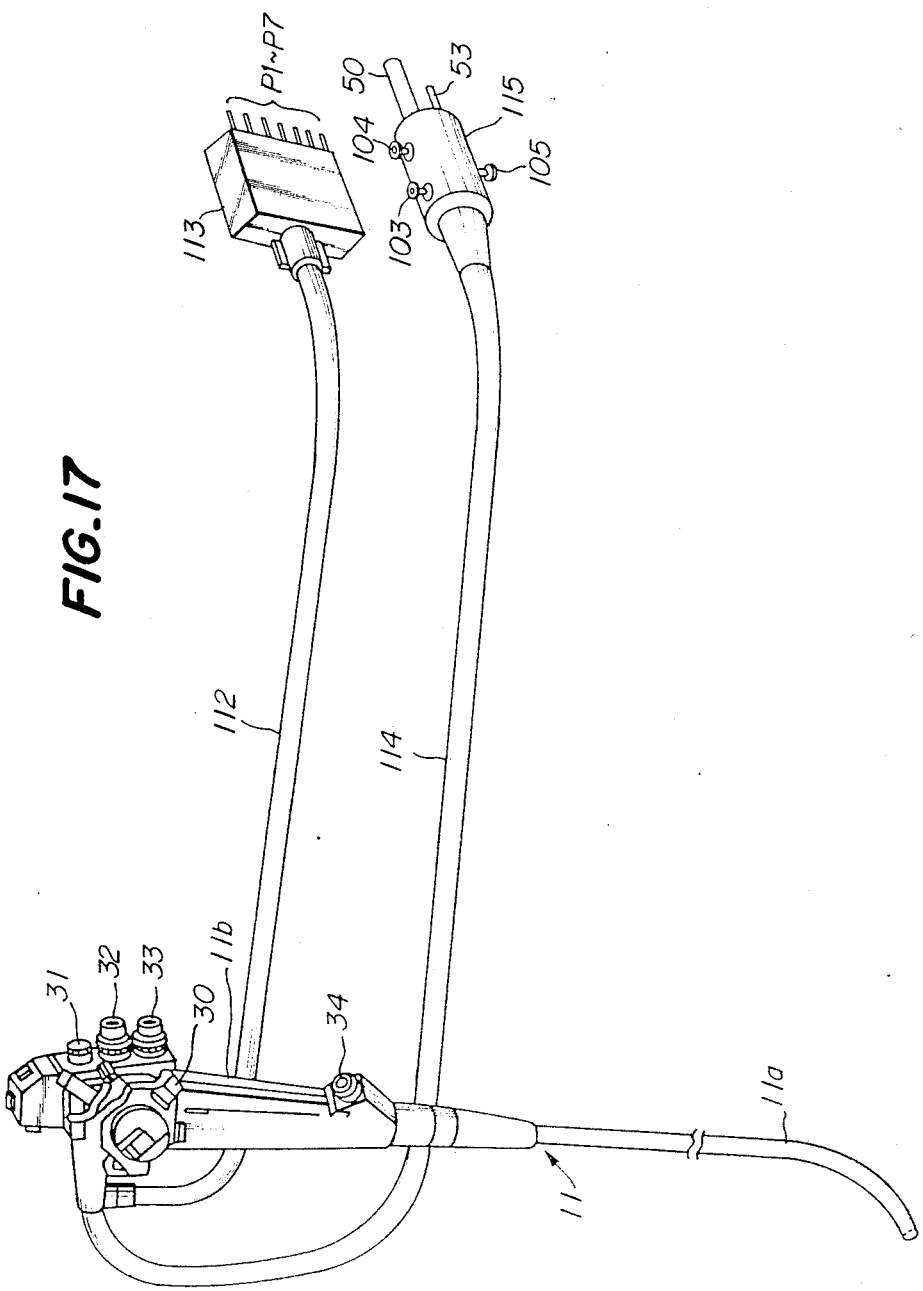
FIGS. 17, 18, 19, and 20 are views showing connectors used in the video scope system shown in FIG. 15.

FIG. 17 shows a construction of a modification of the connector used in the embodiment shown in FIG. 15. The constructions of the video processor 16 and the light source unit 19 are the same as in the embodiment shown in FIG. 15. In this modification, a cable 112 including only a conductor bundle is extended from the handle section 11b of the video scope 11 to the connector 113, and a universal cable 114 including the light guide 50, the water supply tube, and the air supply tube is extended to the connector 115.

Figure 18:
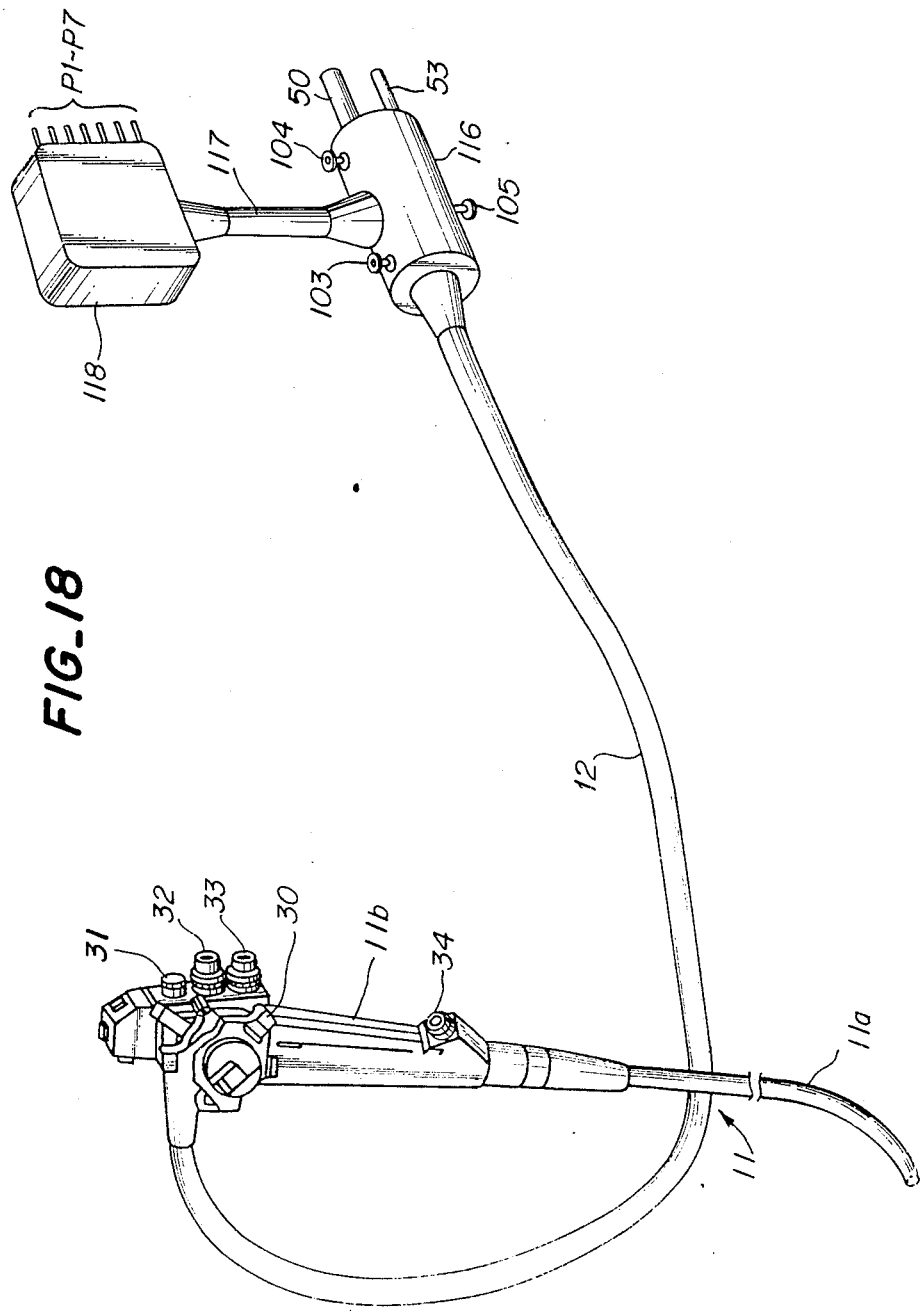

FIG. 18 shows a further modification of the connector used in the embodiment shown in FIG. 15. In this modification, the connector 116 is connected to the universal cable 12 extending from the handle section 11b of the video scope 11, and the connector 118 is connected to the connector 116 through a cable 117 having a certain flexibility. Only the conductor bundle is extended in the cable 117, and the electrical connection is made by the connector 118. The connector 116 makes the connection between the light guide 50 and the air supply tube 53.

Figure 19:
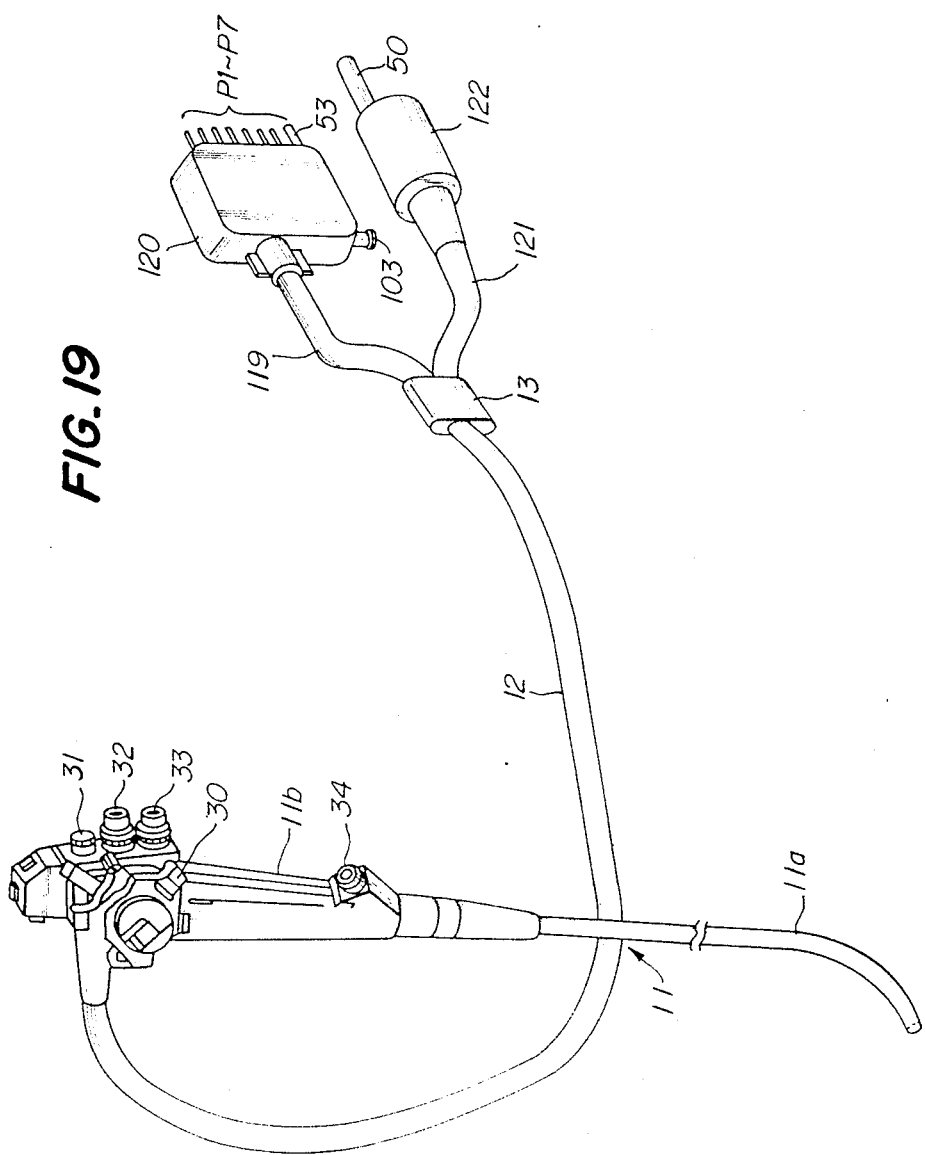

FIG. 19 shows a further modification of the connector of FIG. 15. In this modification, the branch section 13 is connected to the universal cable 12 extending from the handle section 11b of the video scope 11, and the cable 119 extending from the branch section is connected to the connector 120. The conductor bundle and the air and water supply tubes are provided in the cable 119, to make the electrical and hydraulic connections. Another cable 121 is extended from the branch section 13 and connected to the connector 122. The light guide 50 is extended in the cable 121.

Figure 20:
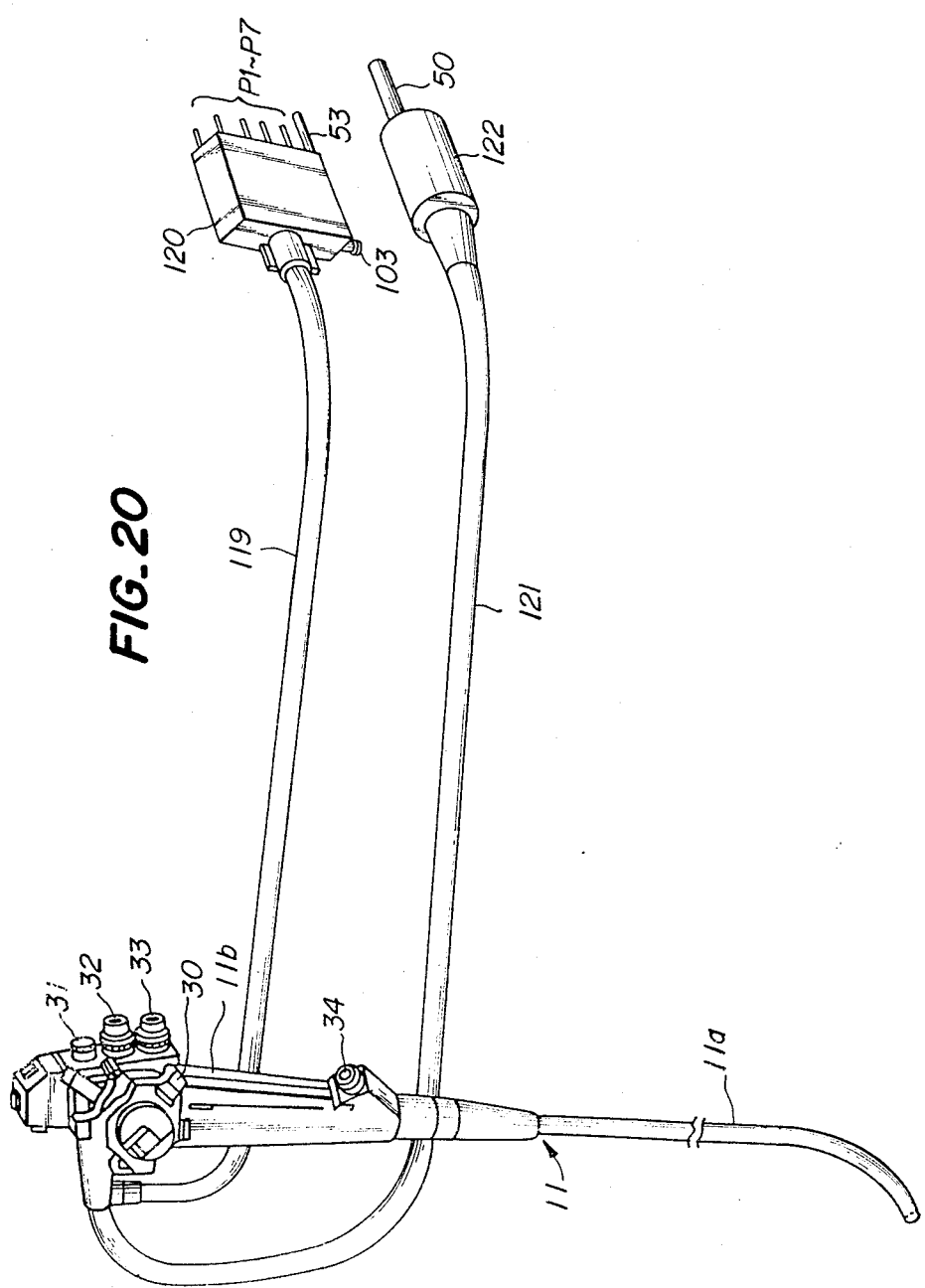

FIG. 20 shows a still further modification of the connector of FIG. 15. In this modification cable 119 including the conductor bundle and the air and water supply tubes is extended from the handle section 11b of the video scope 11, and a connector 120 is connected to an end of the cable 119. A cable 121 including the light guide 50 is also extended from the handle section 11b, and a connector 122 is connected to an end of the cable 121.

Figure 21:
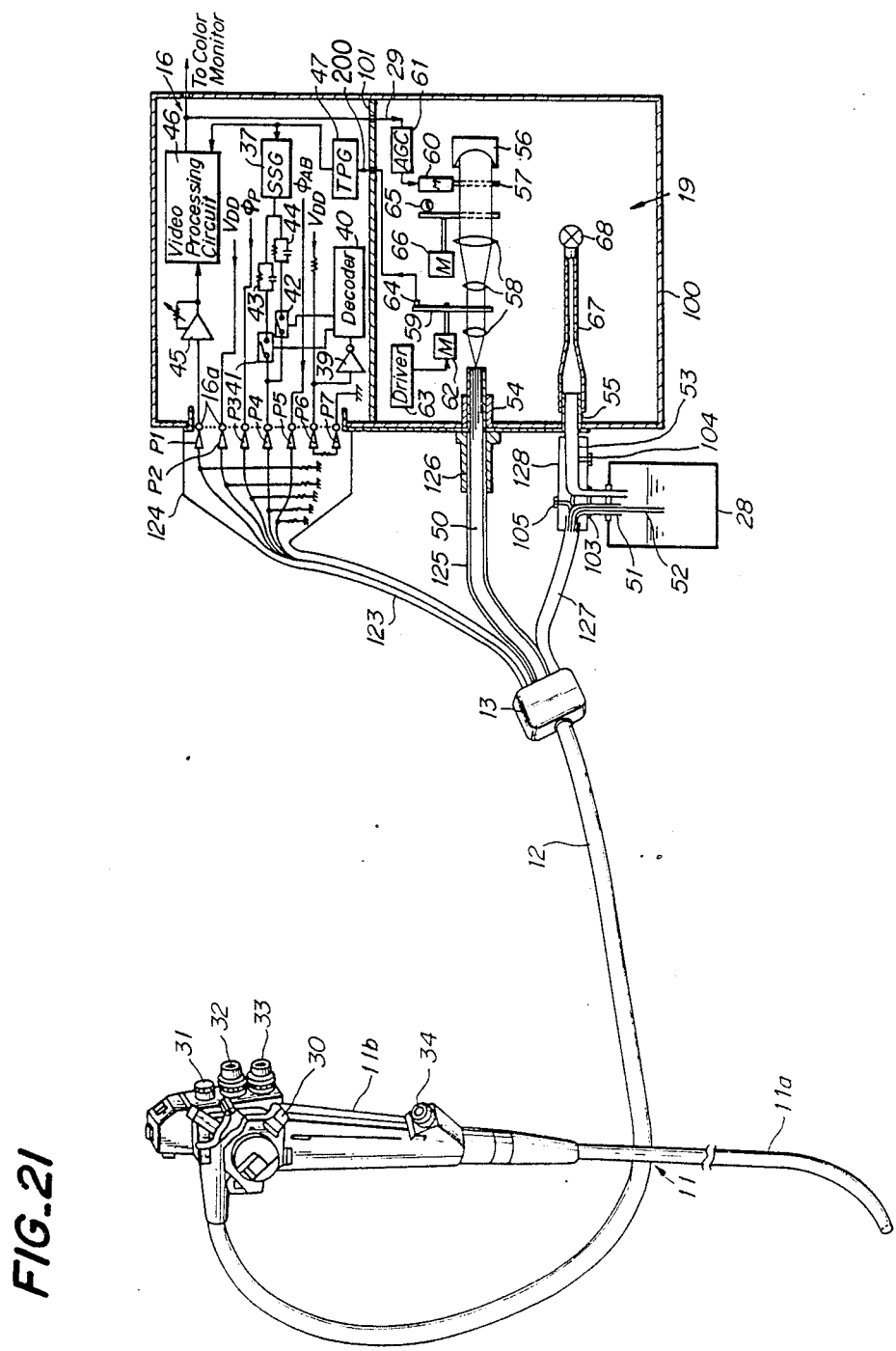
FIG. 21 is a view showing a construction of a seventh embodiment of the video scope system according to the present invention.
Figure 22:
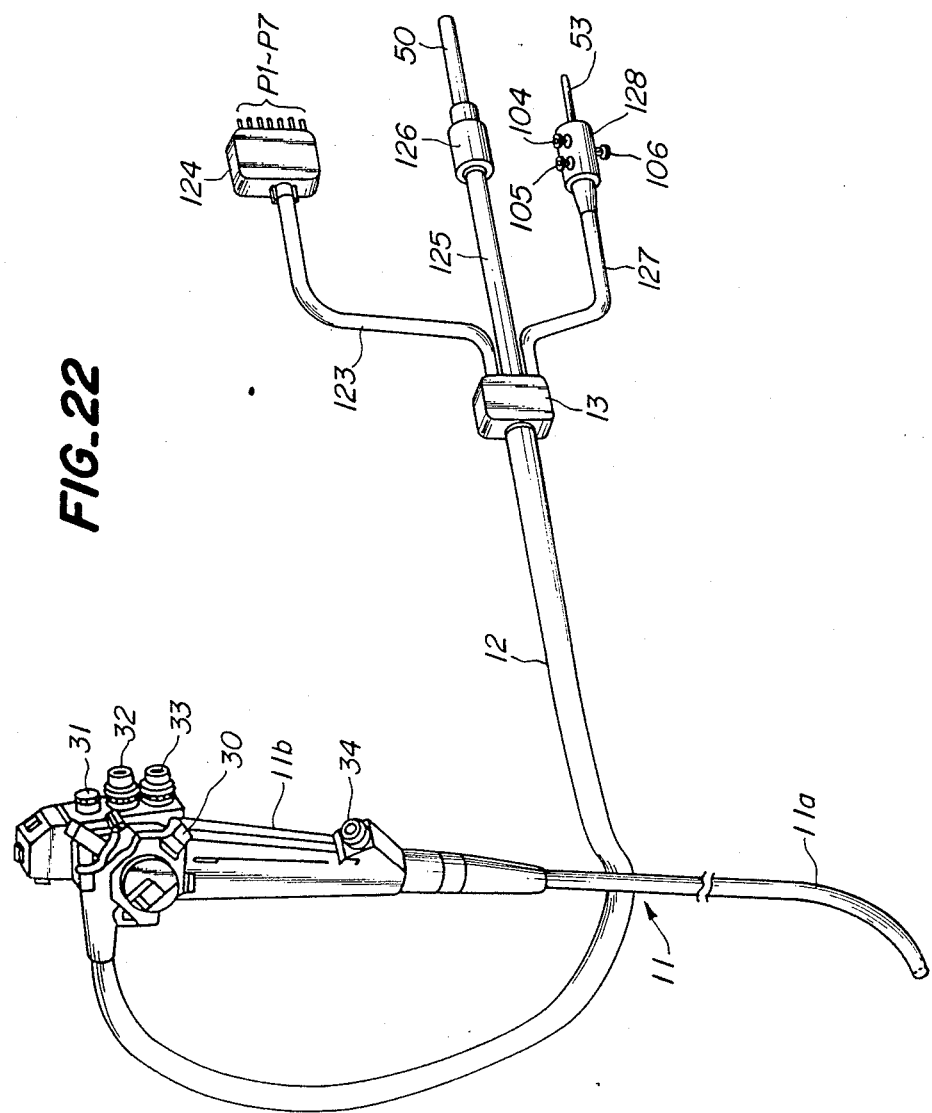
FIG. 22 is a view showing a construction of a connector of the seventh embodiment shown in FIG. 22.

FIGS. 21 and 22 show a seventh embodiment of the video scope system according to the present invention. The construction of inside of the housing 100 is the same as that of the embodiment shown in FIG. 15. In this embodiment, the universal cable 12 extending from the handle section 11b of the video scope 11 is connected to the branch section 13, from which a cable 123 including the conductor bundle is extended, and a connector 124 is connected to an end of the cable 123. A cable 125 including the light guide 50 is extended from the branch section 13, and a connector 126 is connected to the cable 125. A cable 127 including the air and water supply tube is extended from the branch section 13, and a connector 128 is connected to the cable 127. Thus, in this embodiment, the electrical connector 124, the optical connector 126, and the hydraulic connector 128 are separated. The mouthpiece 103 connected to the water supply pump, the mouthpiece 104 connected to the inert gas cylinder, and the mouthpiece 105 connected to the suction device are provided on the connector 128.

Figure 23:
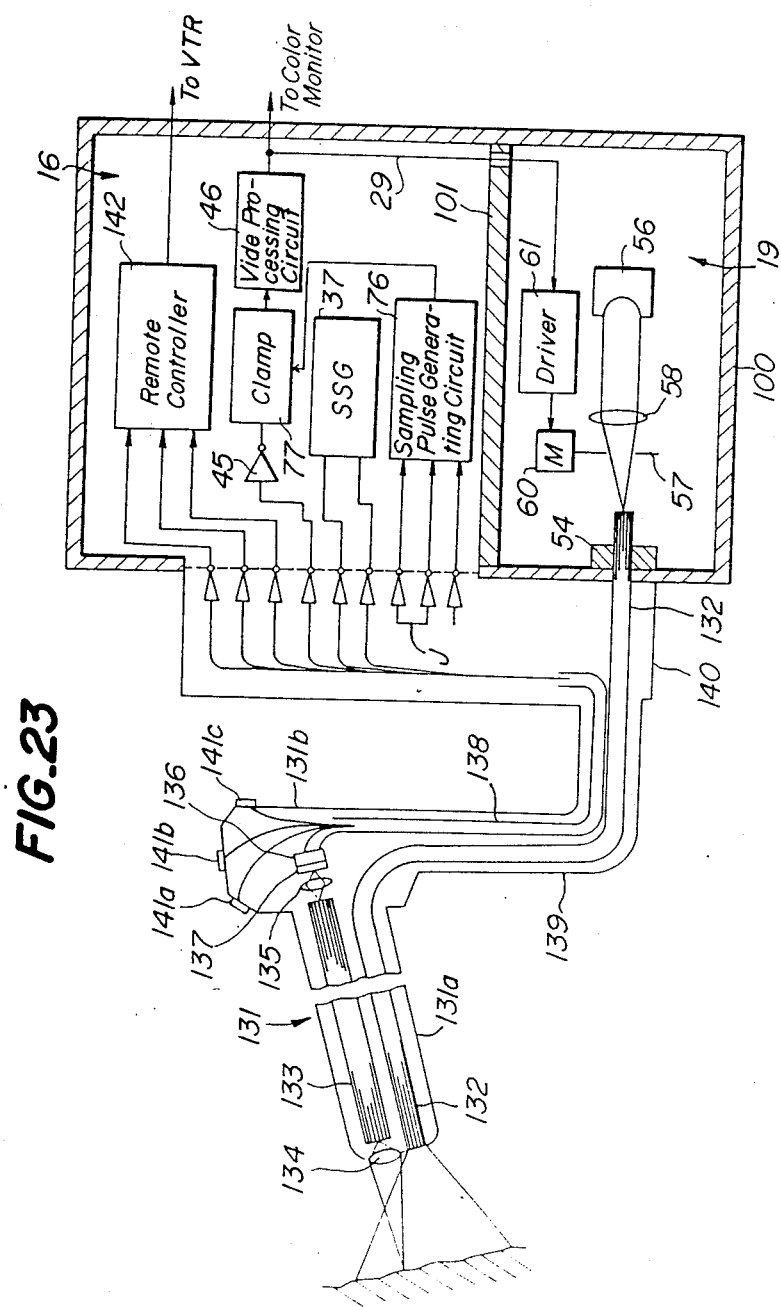
FIG. 23 is a view showing a construction of an eighth embodiment of the video scope system according to the present invention.

Although in the embodiments described above, the CCD image sensor is disposed in the distal end of the insertion section of the video scope, the present invention is not restricted to such a construction. For example, the image sensor may be disposed in the handle section, so that an image picked up by the image guide at the distal end of the insertion section is transmitted to the image sensor. FIG. 23 shows a construction of an eighth embodiment of the video scope system according to the present invention in which the image sensor is assembled in the handle section. The construction of this embodiment is the same as that of the embodiment shown in FIG. 7, except that the video scope 131, the video processor unit 16, and the light source unit 19 are housed in one housing 100. In this embodiment, light guide 132 and an image guide 133 are extended in an insertion section 131a of video scope 131, and an object lens 134 is disposed at the distal end of the insertion section, facing the incident end face of the image guide, so that an image of an object under inspection is formed on the incident end face. Further, an imaging lens 135 is provided in a handle section 131b, facing a light exit end face of the image guide 133, so that an image transmitted in the image guide is made incident upon a solid state CCD image sensor 136. A mosaic color filter 137 in which red, blue and green filters are appropriately distributed is disposed on a front surface of the image sensor 136, and a color image is displayed by a simultaneous color television system. A conductor bundle 138 for supplying a driving signal to the image sensor 136, and supplying a picture signal from the image sensor to the video processor unit, is connected to a socket 140 through a universal cable 139. The housing 100 is separated by the shielding plate 101, so that the video processor unit 16 is disposed in the upper portion and the light source unit 19 is disposed in the lower portion thereof. An output of the video process circuit 46 is supplied to the automatic gain control circuit 61 through the cable 29 extending through the shielding plate 101. Leads in the conductor bundle 138 connected to the image sensor 136 are connected to the standard signal generating circuit 37 for driving the CCD image sensor, and to the pre-amplifier 45. In this embodiment, operation switches 141a through 141c used for a remote-control of the VTR recording of a picture image picked up by the image sensor are provided in the handle section 131b of the video scope 131. Namely, leads connected to these switches are connected to a remote-control unit, and accordingly, the starting and stopping of the VTR operation, and a picture freeze operation can be carried out by remote-control.

Figure 24:
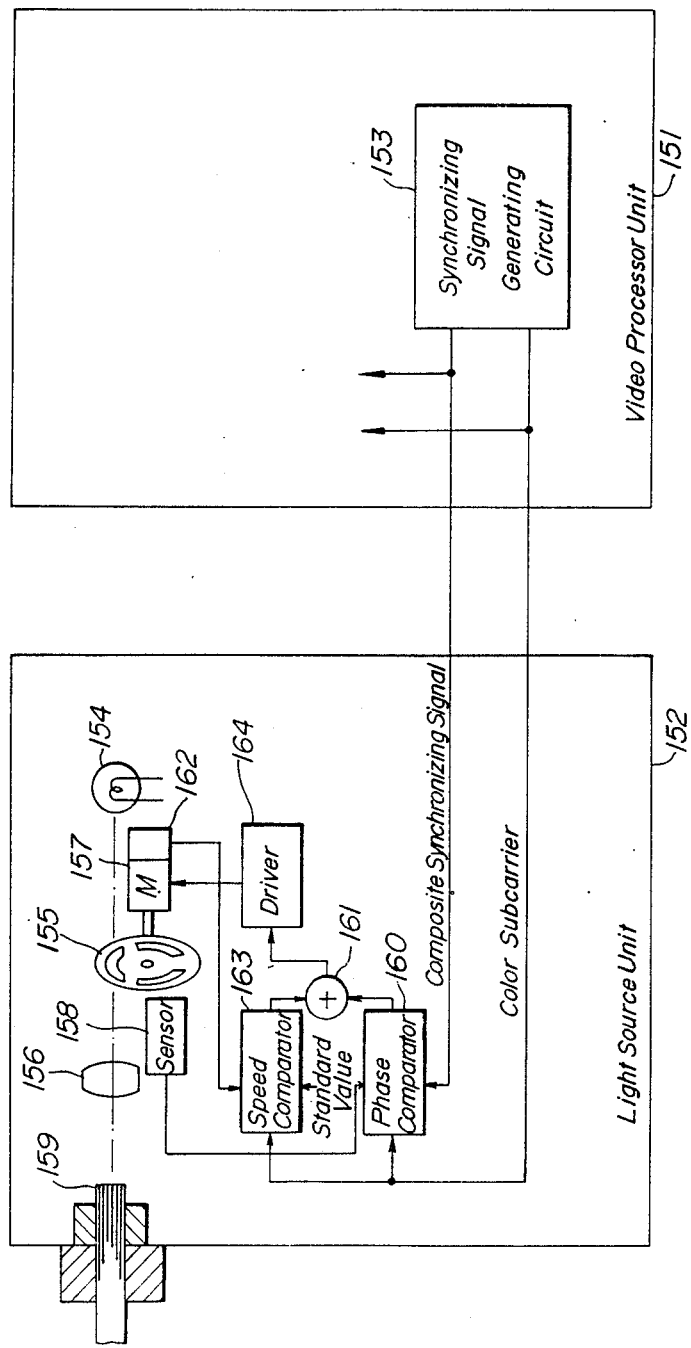
FIG. 24 is a view showing a construction of another example of the light source unit of the present invention.

If a color picture of a field or frame sequential system is displayed by the rotary filter 59 in the embodiments described above, and as shown in FIG. 4, the rotary filter 59 is provided with the marks 59b representing the position of each color filter, the marks are sensed by the sensor 64 including the photo reflector, and the sensed output is supplied to the timing pulse generating circuit 47 so that a driving signal for the image sensor in synchronization with a rotation phase of the rotary filter is generated, and thus a signal process is carried out. But, in the present invention, the system can be constructed in such a manner that a synchronizing signal generating circuit is provided in the video processor unit, so that the rotary filter is driven in synchronization with the synchronizing signal. FIG. 24 shows such an embodiment. In FIG. 24, a part of a video processor unit 151 and a light source unit 152 are shown, wherein synchronizing signal generating circuit 153 is provided in the video processor unit 151, so that a composite synchronizing signal including horizontal and vertical synchronizing signals are supplied to the CCD drive circuit and video processing circuit provided in the video processor unit 151, and to the light source unit 152. The light source unit 152 is provided with a light source lamp 154, a rotary filter 155, a lens 156, a motor 157 for rotating the rotary filter, and a sensor 158 for sensing a rotation phase of the rotary filter. The constructions of these components are the same as the constructions shown in FIGS. 3 and 4, and thus an illuminating light can be fed into an incident end face of the light guide 159 attached to the light source unit 152. In this embodiment, to rotate the rotary filter 155 in synchronization with the vertical synchronizing signal generated by the synchronizing signal generating circuit 153, the composite synchronizing signal is supplied to one input terminal of a phase comparator 160, and rotation position sensing signal of the rotary filter 155 transmitted from the sensor 158 is supplied to the other input terminal of the phase comparator 160. The color sub-carrier is supplied to the phase comparator 160 as a clock pulse, so that a phase difference between a vertical synchronizing signal in the composite synchronizing signal and the rotation position sensing signal of the rotary filter is obtained by counting the color sub-carrier clocks, and then a voltage value corresponding to the counted value is supplied to an adder 161.

An encoder 162 is connected to the motor 157 for driving the rotary filter 155, and an output signal of the encoder is supplied to a velocity comparator 163. The velocity comparator 163 counts a difference between speed of revolution of the motor 157 sensed by the encoder 162 and a predetermined standard speed by using the color sub-carrier as a clock pulse, so that a voltage corresponding to the count value is supplied to the adder 161. Therefore, a control voltage corresponding to the sum of the rotation phase error and the speed of rotation error is produced from the adder 161. This output signal is supplied to a motor driver 164, and the motor 157 is controlled so that the error is eliminated, i.e., is made zero. Thus, the rotary filter 155 provided in the light source unit 152 is rotated in synchronization with a composite synchronizing signal supplied from the synchronizing signal generating circuit 153 provided in the video processor unit 151.

Figure 25:
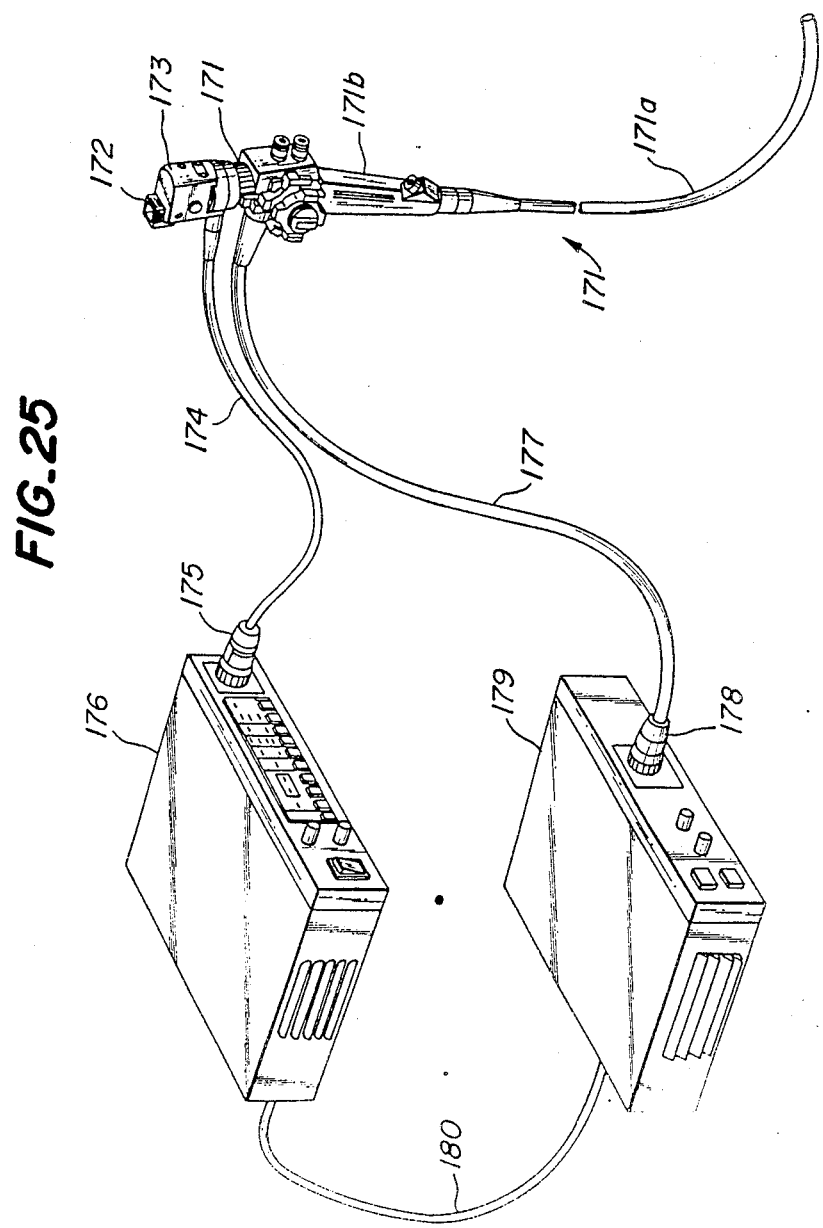
FIG. 25 is a view showing a construction of a ninth embodiment of the video scope system according to the present invention.

FIG. 25 shows a ninth embodiment of the video scope system according to the present invention. In this embodiment, an attachment 173 having a solid state CCD image sensor and an electronic view finder 172 is detachably attached to an eyepiece 171c provided on a handle section 171b of a usual optical scope 171, in the insertion section 171a of which are extended the light guide and the image guide. The attachment 173 is connected to a video processor unit 176 through a cable 174 and a socket 175. Further, the light guide extending from the handle section 171c of the optical scope 171 is connected to a light source unit 179 through a cable 177 and a socket 178. The video processor unit 176 and the light source unit 179 are connected to each other by a cable 180. Also, in this embodiment, since the video processor unit 176 and the light source unit 179 are housed in separate housings, respectively, any adverse influence on the video processor unit of heat generated by the light source unit is effectively prevented.

A plurality of video processor units corresponding to a plurality of video scopes can be used by connecting selected units to connectors of the video scopes to be used. A color television signal from the video processing circuit may be transmitted to the light source unit by an electrical connection similar to a signal transmission between the video processor unit and the light source unit, and supplied to the color monitor through the light source unit. According to this construction, when the video processor unit must be replaced, a switching operation between the video processor unit and the color monitor is not necessary, and a single monitor can be commonly used for a plurality of video processor units corresponding to a plurality of video scopes. Further, although a solid state CCD image sensor is used as the image sensor in the embodiments described above, a solid state image sensor such as a BBD, SIT and the like can be used. Further, although in the embodiments described above, a color picture is displayed, a black and white picture also can be displayed. In this case, the rotary filter and the mosaic filter can be omitted. In the embodiment in which the video processor unit and the light source unit are housed in a common housing and separated by the shielding plate, the video processor unit and the light source unit can be mounted on boards, respectively, so that these boards are housed in the housing. Also, in this case, the replacement of the units is easily carried out.

According to the video scope system of the present invention described above, since the video processor unit and the light source unit are separated by the shielding means, and these units are connected to each other by an electrical cable, any adverse influence of heat generated by the light source lamp provided in the light source unit on the electronic circuits of the video processor unit is effectively prevented.

In the embodiment in which the video processor unit and the light source unit are housed in different housings, respectively, if a malfunction of one of the units occurs, the malfunctioning unit can be easily and quickly replaced by a new unit, which effectively reduces the running costs.

In the embodiment in which the connectors for the video processor unit and the light source unit are constructed as separate components, the constructions of the connectors are simplified, and the connecting and disconnecting operations become easy, and further, the possibility of damage to the connectors is reduced.

In the embodiment in which the video processor unit and the light source unit are connected to each other by the connector, since the cable for connecting these units can be omitted, the handling of the connector becomes easier, and the construction of the connector is simplified.

Although embodiments of the present invention have been described herein with reference to the attached drawings, many modifications and changes may be made by those skilled in this art without departing from the scope of the invention.

What is claimed is:

1. A video scope system for picking up an image of an object under inspection, said image being formed by an optical system disposed at a distal end of an insertion section inserted in said object under inspection, said video scope system comprising;
    a video scope comprising said insertion section, an image sensor for picking up said image of said object under inspection, a conductor connected to said image sensor, a first connector connected to said conductor, a light guide extending through said insertion section and having a light incident end, and a second connector holding said light incident end;
    a light source unit having a first socket detachably connected to said second connector, and feeding an illumination light into said light guide;
    a video processor unit having a second socket detachably connected to said first connector, said video processor unit providing a driving signal for said image sensor, and processing an image signal supplied from said image sensor;
    a shielding means for thermally shielding said light source unit and said video processor unit from each other; and
    an electrical connecting means for transmitting a signal between said light source unit and said video processor unit.

2. A video scope system according to claim 1, wherein said shielding means thermally and electrically shields said light source unit and said video processor unit from each other.

3. A video scope system according to claim 2, wherein said shielding means comprises a first housing enclosing said light source unit, and a second housing enclosing said video processor unit separately from said first housing, said electrical connecting means having an electric lead for transmitting a signal between said first housing and said second housing.

4. A video scope system according to claim 2, wherein said shielding means comprises a common housing enclosing said light source unit and said video processor unit, and a shielding plate disposed between said light source unit and said video processor unit in said common housing, said electrical connecting means having an electric lead extending through said shielding plate.

5. A video scope system according to claim 1, wherein said image sensor of said video scope is disposed in said distal end of said insertion section.

6. A video scope system according to claim 1, wherein said video scope comprises an image guide extending through said insertion section, said image sensor being provided in a proximal end of said image guide to pick up an image of said object under inspection, which image is transmitted through said image guide.

7. A video scope system according to claim 6, wherein said video scope comprises an eyepiece section for observing said image of said object under inspection transmitted through said image guide, said image sensor being disposed in an attachment detachably mounted on said eyepiece.

8. A video scope system according to claim 1, wherein said image sensor comprises a solid state image sensor having a plurality of light receiving elements arranged in matrix.

9. A video scope system according to claim 1, wherein said light source unit comprises a variable stop disposed in an optical path of the illumination light, means for driving said variable stop, and a drive circuit generating a driving signal for said driving means, said electrical connecting means having a lead connecting said drive circuit to an output terminal of a video processor circuit of said video processor unit, to control said variable stop so that an image signal supplied from said video process circuit has an approximately constant amplitude.

10. A video scope system according to claim 1, wherein a mosaic color filter is disposed on a front surface of said image sensor.

11. A video scope system according to claim 1, wherein said light source unit comprises a rotary filter having at least two color filter sectors, a motor rotating said rotary filter at a constant speed in synchronization with a field synchronizing signal, means for sensing a rotational phase of said rotary filter to generate a color discriminating signal, said video processor unit being provided with a timing pulse generating circuit generating a driving signal for said image sensor, and said electrical connecting means including a lead controlling said timing pulse generating circuit to supply said color discriminating signal to said timing pulse generating circuit to generate a driving signal synchronized with a rotational phase of said rotary filter.

12. A video scope system comprising:
a video scope having an insertion section to be inserted into a cavity of an object under inspection, an optical system disposed in a distal end of said insertion section, a light guide extending in said insertion section and having a front end provided in said distal end and a rear end provided outside of said insertion section, an image sensor for picking up an image of said object under inspection formed by said optical system;
an optical connector connected to said rear end of said light guide;
an electrical lead connected to said image sensor;
an electrical connector connected to an end of said electrical lead;
a light source unit having a socket receiving said optical connector, a light source device emitting an illumination light, a rotatable color filter through which said illumination light passes and an optical system feeding said illumination light to said rear end of said light guide;
a video processor unit having a socket receiving said electric connector, a drive circuit generating a driving signal to be supplied to said image sensor, and a video processing circuit receiving an output signal from said image sensor to generate a color image signal to be displayed on a monitor;
a second housing enclosing said video processor unit;
an electrical connecting means provided between said light source unit and said video processor unit to transmit a signal from said video processor unit to said rotatable color filter in said light source unit to synchronize operation of said rotatable color filter with said color image signal; and
said electric connecting means comprising a lead transmitting a signal, a first and a second signal connectors connected to both ends of said lead, and a first and a second signal sockets provided in said first housing and said second housing and detachably connected to said first and second signal connectors, respectively.

13. A video scope system according to claim 12, wherein said image sensor of said video scope is disposed in said distal end of said insertion section.

14. A video scope system according to claim 12, wherein said video scope comprises an image guide extending through said insertion section, said image sensor being provided in a proximal end of said image guide to pickup an image of said object under inspection transmitted through said image guide.

15. A video scope system according to claim 14, wherein said video scope comprises an eyepiece section for observing said image of said object under inspection transmitted through said image guide, said image sensor being disposed in an attachment detachably mounted on said eyepiece section.

16. A video scope system according to claim 12, wherein said electrical lead and light guide are provided in a universal cable, said optical connector and said electrical connector are provided in a single casing, and said universal cable is connected to said casing.

17. A video scope system according to claim 16, wherein said lead of said electrical connecting means is fixed in said single casing, and said first and second signal connectors are provided in said single casing.

18. A video scope system according to claim 12, wherein said electrical lead and said light guide are provided in a universal cable, which is connected to a branch member, said light guide being connected to said optical connector through a first cable from said branch member, and said electrical lead being connected to said electrical connector through a second cable from said branch member.

19. A video scope system comprising:
a video scope having an insertion section to be inserted into a cavity of an object under inspection, an optical system disposed in a distal end of said insertion section, a light guide extending in said insertion section and having a front end provided in said distal end and a rear end provided outside said insertion section, an image sensor picking up an image of said object under inspection formed by said optical system;

an optical connector connected to said rear end of said light guide;

an electrical lead connected to said image sensor;

an electrical connector connected to an end of said electrical lead;

a light source unit having a socket receiving said optical connector, a light source device emitting an illumination light, and an optical system feeding said illumination light to said rear end of said light guide;

a video processor unit having a socket receiving said electrical connector, a drive circuit generating a driving signal supplied to said image sensor, a video processing circuit receiving an output signal from said image sensor to generate an image signal to be displayed on a monitor;

a single housing enclosing said light source unit and said video processor unit;

a shielding plate disposed in said housing, and thermally and electrically shielding said light source unit and said video processor unit from each other; and an electrical connecting means provided between said light source unit and said video processor unit to transmit a signal therebetween.

20. A video scope system according to claim 19, wherein said image sensor of said video scope is disposed in said distal end of said insertion section.

21. A video scope system according to claim 19, wherein said video scope has an image guide extending in said insertion section, said image sensor being provided in a proximal end of said image guide to pick up an image of said object under inspection transmitted through said image guide.

22. A video scope system according to claim 21, wherein said video scope comprises an eyepiece section for observing said image of said object under inspection transmitted through said image guide, said image sensor being disposed in an attachment detachably mounted on said eyepiece section.

23. A video scope system according to claim 19, wherein said electrical lead and said light guide are provided in a universal cable, said optical connector and said electrical connector are provided in a single casing, and said universal cable is connected to said single casing.

* * * * *